United States Patent [19]

Hino et al.

[11] Patent Number: 5,021,421
[45] Date of Patent: Jun. 4, 1991

[54] 2-(1-PIPERAZINYL)-4-PHENYLCYCLOALK-ANOPYRIDINE DERIVATIVES, PROCESSES FOR THE PRODUCTION THEREOF, AND PHARMACEUTICAL COMPOSITION CONTAINING THE SAME

[75] Inventors: Katsuhiko Hino, Nara; Naoki Kai, Amagasaki; Masato Sakamoto, Toyonaka; Tatsuya Kon, Ashiya; Makoto Oka, Ibaraki; Kiyoshi Furukawa, Shiga; Yoshiaki Ochi, Toyonaka, all of Japan

[73] Assignee: Dainippon Pharmaceutical Co., Ltd., Osaka, Japan

[21] Appl. No.: 481,183

[22] Filed: Feb. 20, 1990

[30] Foreign Application Priority Data

Mar. 3, 1989 [JP] Japan .................. 1-52544

[51] Int. Cl.⁵ .................. A61K 31/495; C07D 401/04
[52] U.S. Cl. .................. 514/254; 514/218;
540/575; 544/295; 544/361; 544/362; 544/363
[58] Field of Search ............... 540/575; 544/361, 362, 544/363, 295; 514/218, 254

[56] References Cited

U.S. PATENT DOCUMENTS 4,469,696 9/1984 Rosentreter et al. .............. 544/360
4,831,034 5/1989 Barreau et al. .................. 514/255

Primary Examiner—Cecilia Shen
Attorney, Agent, or Firm—Birch, Stewart, Kolasch & Birch

[57] ABSTRACT

Novel 2-(1-piperazinyl)-4-phenyl-cycloalkanopyridine derivatives of the formula (I):

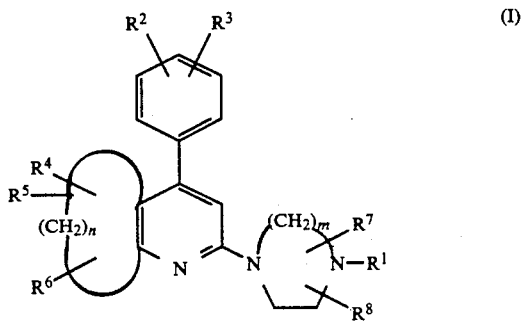

wherein n is 3, 4, 5, 6 or 7; $R^1$ is a hydrogen atom, $C_1$-$C_{10}$ alkyl, $C_2$-$C_6$ alkenyl, $C_2$-$C_6$ alkynyl, $C_3$-$C_8$ cycloalkyl, $C_3$-$C_6$ cycloalkyl-($C_1$-$C_4$) alkyl, hydroxy-($C_2$-$C_6$) alkyl, $C_1$-$C_3$ alkoxy-($C_2$-$C_6$) alkyl, acyloxy-($C_2$-$C_6$), alkyl, unsubstituted or substituted aroyl-($C_1$-$C_6$) alkyl, unsubstituted or substituted aryl, heteroaryl, or acyl; $R^2$ and $R^3$ are the same or different and are each a hydrogen atom, a halogen atom, $C_1$-$C_6$ alkyl, $C_1$-$C_6$ alkoxy, trifluoromethyl, or hydroxy; $R^4$, $R^5$ and $R^6$ are the same or different and are each a hydrogen atom, $C_1$-$C_6$ alkyl, or phenyl, or two of $R^4$, $R^5$ and $R^6$ combine to form a single bond or $C_1$-$C_3$ alkylene; $R^7$ and $R^8$ are the same or different and are each a hydrogen atom or $C_1$-$C_3$ alkyl; m is 2 or 3, or an acid addition salt thereof, which is useful as a psychotropic drug, and processes for the preparation thereof.

19 Claims, No Drawings

2-(1-PIPERAZINYL)-4-PHENYLCYCLOALK-ANOPYRIDINE DERIVATIVES, PROCESSES FOR THE PRODUCTION THEREOF, AND PHARMACEUTICAL COMPOSITION CONTAINING THE SAME

This invention relates to novel 2-(1-piperazinyl)-4-phenylcycloalkanopyridine derivatives having psychotropic activity, processes for the production thereof, and a pharmaceutical composition containing the said compound as an active ingredient.

PRIOR ART

There have hitherto been known some 2-(1-piperazinyl)-4-arylpyridine derivatives and related compounds which have pharmacological activities. For example, U.S. Pat. No. 4,469,696 [Japanese First Publication (Kokai) No. 58-963] discloses 2-(1-piperazinyl)-4-arylpyridine derivatives, however, the compounds disclosed therein are merely the compounds having an aryl group or a 2-furyl group at 5-position of pyridine ring, structure of which is completely different from that of the compounds of the present invention. Besides, the pharmacological activity of these compounds disclosed in the above reference is lipid absorption-inhibitory action which is also completely different from that of the compounds of the present invention. It is clear from the experiments by the present inventors, whereby the 4,5-bis-(4-fluorophenyl)-6-methyl-2-(4-phenyl-1-piperazinyl)pyridine disclosed in the above mentioned U.S. patent did not show any psychotropic activity, that is, it shows no inhibitory effect on an apomorphine-induced vomiting, which can be an index for antipsychotic drug and no binding property to dopamine ($D_2$) and serotonin ($S_2$) receptors.

Moreover, a pyridine derivative having a piperazinyl group and a phenyl group at 2-position and 4-position of pyridine ring thereof respectively, 2-[4-(4-methylbenzyl)-1-piperazinyl]-4-phenylpyridine has been reported to have a weak activity as an anti-psychotic drug or as a neuroleptic drug, [cf: U.S. Pat. No. 4,831,034, Japanese First Publication (Kokai) No. 63-48267]. However, the structure of this compound is obviously different from that of the compounds of the present invention in respect to that this compound does not form the condensed ring between 5- and 6-positions of pyridine ring.

BRIEF DESCRIPTION OF THE INVENTION

The present inventors have extensively searched for compounds having an activity on the central nervous system and have found that novel 2-(1-piperazinyl)-4-phenylcycloalkanopyridine derivatives of the formula (I) disclosed hereinafter have excellent psychotropic activity and are useful as an anti-psychotic drug or an anti-anxiety drug and further as a drug for the treatment of cerebral insufficiency diseases.

An object of the invention is to provide novel 2-(1-piperazinyl)-4-phenylcycloalkanopyridine derivatives having excellent psychotropic activity. Another object of the invention is to provide processes for the production of these compounds. A further object of the invention is to provide a pharmaceutical composition being useful as an anti-psychotic or anti-anxiety drug etc. containing said compound as an active ingredient. These and other objects and advantages of the invention will be apparent to those skilled in the art from the following description.

DETAILED DESCRIPTION OF THE INVENTION

The novel 2-(1-piperazinyl)-4-phenylcycloalkanopyridine derivatives of the present invention have the following formula (I):

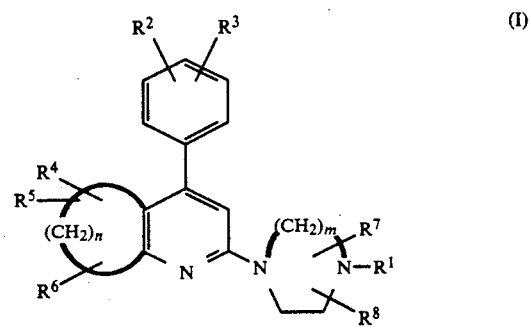

wherein n is 3, 4, 5, 6 or 7, $R^1$ is a hydrogen atom, $C_1$–$C_{10}$ alkyl, $C_2$–$C_6$ alkenyl, $C_2$–$C_6$ alkynyl, $C_3$–$C_8$ cycloalkyl, $C_3$–$C_6$ cycloalkyl-($C_1$–$C_4$)alkyl, hydroxy-($C_2$–$C_6$) alkyl, $C_1$–$C_3$ alkoxy-($C_2$–$C_6$) alkyl, acyloxy-($C_2$–$C_6$) alkyl, unsubstituted or substituted aroyl-($C_1$–$C_6$) alkyl, unsubstituted or substituted aryl, heteroaryl, or acyl, $R^2$ and $R^3$ are the same or different and are each a hydrogen atom, a halogen atom, $C_1$–$C_6$ alkyl, $C_1$–$C_6$ alkoxy, trifluoromethyl, or hydroxy, $R^4$, $R^5$ and $R^6$ are the same or different and are each a hydrogen atom, $C_1$–$C_6$ alkyl, or phenyl, or two of $R^4$, $R^5$ and $R^6$ combine to form a sigle bond or $C_1$–$C_3$ alkylene, $R^7$ and $R^8$ are the same or different and are each a hydrogen atom or $C_1$–$C_3$ alkyl, m is 2 or 3, or an acid addition salt thereof.

The salt of the compounds of the formula (I) includes salts of inorganic acids (e.g. hydrochloride, hydrobromide, hydroiodide, sulfate, phosphate, etc.), and salts of organic acids (e.g. maleate, fumarate, citrate, oxalate, tartrate, lactate, benzoate, methanesulfonate, etc.). Besides, these salts may optionally be present in the form of a hydrate, and hence, the compounds of the present invention include also these hydrate compounds.

Besides, when the compounds of the formula (I) contain asymmetric carbons, these compounds include stereoisomers, a mixture thereof, and a racemic mixture, which are also included as the active compound in the present invention.

In the present specification and claims, the groups in the formulae denote the following groups.

The "alkyl" and "alkyl moiety" and "alkylene" include straight chain or branched chain alkyl groups or alkylene groups.

The "alkyl" includes methyl, ethyl, propyl, isopropyl, butyl, isobutyl, sec-butyl, pentyl, isopentyl, neopentyl, hexyl, isohexyl, heptyl, octyl, nonyl, decyl, and the like.

The "alkylene" includes methylene, ethylene, propylene, and the like.

The "halogen atom" includes fluorine, chlorine, bromine, and iodine.

The "alkoxy" includes methoxy, ethoxy, propoxy, isopropoxy, butoxy, isobutoxy, pentyloxy, hexyloxy, and the like.

The "cycloalkyl" includes, for example, cyclopropyl, cyclobutyl, cyclopentyl, cyclohexyl, cycloheptyl, and the like.

The "cycloalkyl-alkyl" includes cyclopropylmethyl, cycylobutylmethyl, cyclopentylmethyl, and the like.

The "hydroxyalkyl" includes 2-hydroxyethyl, 2-hydroxypropyl, 3-hydroxypropyl, 2,3-dihydroxypropyl, 4-hydroxybutyl, 2-hydroxybutyl, and the like.

The "alkoxyalkyl" includes methoxymethyl, methoxyethyl, ethoxyethyl, and the like.

The "alkenyl" includes vinyl, allyl, 1-propenyl, isopropenyl, 1-butenyl, 2-butenyl, and the like.

The "alkynyl" includes ethynyl, propargyl, and the like.

The "aryl" includes phenyl, naphthyl, and the like. The "unsubstituted or substituted aryl" includes aryl groups having no substituent or one or two substituents selected from halogen atom, $C_1$-$C_3$ alkyl, $C_1$-$C_3$ alkoxy, and trifluoromethyl, and the examples are phenyl, 4-fluorophenyl, and the like.

The "unsubstituted or substituted aroylalkyl" includes aroylalkyl groups in which the aryl moiety is the above-mentioned unsubstituted or substituted aryl, and the examples are benzoylmethyl, p-fluorobenzoylpropyl, and the like.

The "heteroaryl" means a monocyclic or bicyclic heterocyclic group containing at least one hetero atom selected from nitrogen, oxygen and sulfur, for example, furyl, thienyl, pyridyl, pyrimidyl, isoquinolyl, and the like.

The "acyl" includes $C_1$-$C_4$ alkanoyl, $C_5$-$C_6$ cycloalkylcarbonyl, a benzoyl group which may optionally be substituted by halogen, $C_1$-$C_3$ alkyl or $C_1$-$C_3$ alkoxy, a heteroarylcarbonyl group in which the heteroaryl moiety is the above-mentioned heteroaryl, and the examples are formyl, acetyl, propionyl, butyryl, cyclohexanecarbonyl, benzoyl, benzoyl, nicotinoyl, isonicotinoyl, 4-fluorobenzoyl, furoyl, thenoyl, and the like.

The "acyloxyalkyl" includes acyloxyalkyl groups in which the acyl moiety is the above-mentioned acyl, and the examples are 2-acetyloxyethyl, 3-acetoxypropyl, benzoyloxyethyl, and the like.

Among the compounds of the formula (I) of the present invention, preferred compounds are those of the formula (I) wherein $R^1$ is a hydrogen atom, $C_1$-$C_{10}$ alkyl, $C_3$-$C_8$ cycloalkyl, hydroxy-($C_2$-$C_6$) alkyl, $C_1$-$C_3$ alkoxy-($C_2$-$C_4$) alkyl, $C_2$-$C_4$ alkanoyloxy-($C_2$-$C_6$) alkyl, a benzoyl-($C_2$-$C_5$) alkyl group in which the phenyl moiety may optionally be substituted by halogen, $C_1$-$C_3$ alkyl or $C_1$-$C_3$ alkoxy, $C_2$-$C_4$ alkenyl, $C_2$-$C_4$ alkynyl, pyridyl, pyrimidyl, $C_2$-$C_5$ alkanoyl or furoyl, $R^2$ and $R^3$ are the same or different and are each hydrogen atom, halogen atom, methyl or methoxy, $R^4$, $R^5$ and $R^6$ are the same or different and are each a hydrogen atom or $C_1$-$C_4$ alkyl, or two of them combine to form $C_1$-$C_2$ alkylene, $R^7$ and $R^8$ are the same or different, and are each hydrogen atom or $C_1$-$C_3$ alkyl, and m is 2, and an acid addition salt thereof.

Further preferred compounds of the present invention are the compounds of the formula (I) wherein $R^1$ is a hydrogen atom, $C_1$-$C_8$ alkyl, $C_3$-$C_8$ cycloalkyl, hydroxy-($C_2$-$C_6$)alkyl, $C_1$-$C_2$ alkoxy-($C_2$-$C_3$) alkyl, acetyloxy-($C_2$-$C_4$) alkyl, $C_3$-$C_4$ alkenyl, or $C_2$-$C_3$ alkanoyl, $R^2$ and $R^3$ are the same and both are hydrogen atom or halogen atom, or one of them is hydrogen atom and the other is halogen atom, methyl, or methoxy, and an acid addition salt thereof. More preferred compounds of the present invention are the compounds of the formula (I) wherein $R^2$ and $R^3$ are the same or different and are each a hydrogen atom or a fluorine atom, and an acid addition salt thereof.

Particularly preferred compounds are the compounds of the following formula (I-1):

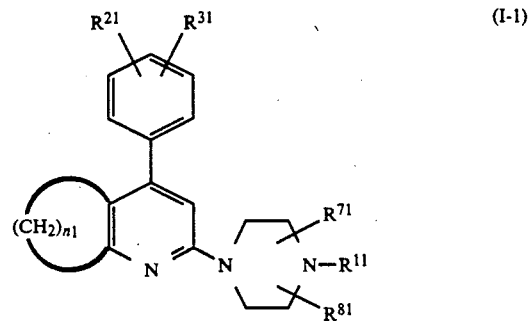

wherein $n_1$ is 3, 6 or 7, $R^{11}$ is hydrogen atom, $C_1$-$C_8$ alkyl, $C_3$-$C_6$ cycloalkyl, hydroxy-($C_2$-$C_4$) alkyl, $C_1$-$C_2$ alkoxy-($C_2$-$C_3$) alkyl, or $C_3$ alkenyl, $R^{21}$ and $R^{31}$ are the same or different and are each a hydrogen atom or a fluorine atom, $R^{71}$ and $R^{81}$ are the same or different and are each a hydrogen atom or $C_1$-$C_3$ alkyl, or an acid addition salt thereof, and of the following formula (I-2):

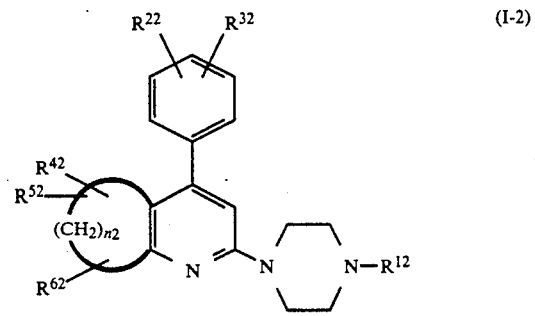

wherein $n_2$ is 4 or 5, $R^{12}$ is a hydrogen atom, $C_1$-$C_8$ alkyl, $C_3$-$C_8$ cycloalkyl, hydroxy-($C_2$-$C_4$) alkyl, $C_1$-$C_2$ alkoxy-($C_2$-$C_3$) alkyl or $C_3$ alkenyl, $R^{22}$ and $R^{32}$ are the same or different and are each a hydrogen atom or a fluorine atom, $R^{42}$, $R^{52}$ and $R^{62}$ are the same or different and are each a hydrogen atom or $C_1$-$C_4$ alkyl, or two of them combine to form $C_1$-$C_2$ alkylene, or an acid addition salt thereof.

Especially most preferred compounds in the present invention are the compounds of the formula (I-1) wherein $n_1$ is 6, $R^{11}$ is $C_1$-$C_6$ alkyl, $C_3$-$C_6$ cycloalkyl, or hydroxy-($C_2$-$C_4$)alkyl, $R^{21}$ and $R^{31}$ are the same or different and are each a hydrogen atom or a fluorine atom substituted at 2- or 4-position, $R^{71}$ and $R^{81}$ are each a hydrogen atom, and a salt thereof, and the compounds of the formula (I-2) wherein $n_2$ is 5, $R^{12}$ is $C_1$-$C_6$ alkyl, $C_3$-$C_6$ cycloalkyl or hydroxy-($C_2$-$C_4$) alkyl, $R^{22}$ and $R^{32}$ are the same or different and are each a hydrogen atom or a fluorine atom substituted at 2- or 4-position, $R^{42}$, $R^{52}$ and $R^{62}$ are all hydrogen atoms, or two of them combine to form $C_1$-$C_2$ alkylene, and another one is a hydrogen atom, and an acid addition salt thereof.

The most preferred compounds of the present invention are the compounds of the following formula (I-3):

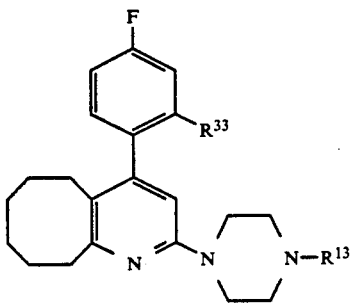

wherein R¹³ is methyl, ethyl, propyl, butyl, pentyl or hydroxyethyl, and R³³ is a hydrogen atom or a fluorine atom, and a salt thereof.

Specifically preferred compounds of the present invention are as follows.

2-(4-Methyl-1-piperazinyl)-4-(4-fluorophenyl)-5,6,7,8,9,10-hexahydrocycloocta[b]pyridine 2-(4-Methyl-1-piperazinyl)-4-(2,4-difluorophenyl)-5,6,7,8,9,10-hexahydrocycloocta[b]pyridine 2-(4-Ethyl-1-piperazinyl)-4-(4-fluorophenyl)-5,6,7,8,9,10-hexahydrocycloocta[b]pyridine 2-(4-Ethyl-1-piperazinyl)-4-(2,4-difluorophenyl)-5,6,7,8,9,10-hexahydrocycloocta[b]pyridine 2-(4-n-Propyl-1-piperazinyl)-4-(4-fluorophenyl)-5,6,7,8,9,10-hexahydrocycloocta[b]pyridine 2-(4-n-Propyl-1-piperazinyl)-4-(2,4-difluorophenyl)-5,6,7,8,9,10-hexahydrocycloocta[b]pyridine 2-(4-n-Butyl-1-piperazinyl)-4-(4-fluorophenyl)-5,6,7,8,9,10-hexahydrocycloocta[b]pyridine 2-(4-n-Pentyl-1-piperazinyl)-4-(4-fluorophenyl)-5,6,7,8,9,10-hexahydrocycloocta[b]pyridine 2-[4-(2-Hydroxyethyl)-1-piperazinyl]-4-(4-fluorophenyl)-5,6,7,8,9,10-hexahydrocycloocta[b]pyridine The compounds of the present invention can be prepared, for example, by the following processes.

(1) Process A

The compounds of the formula (I) are prepared by reacting a compound of the formula (II):

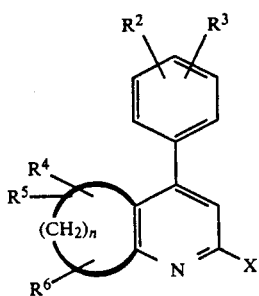

wherein X is a leaving atom or group, and R², R³, R⁴, R⁵, R⁶ and n are as defined above, with a compound of the formula (III):

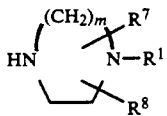

wherein R¹, R⁷, R⁸ and m are as defined above.

The leaving atom or group X in the formula (II) denotes any atom or group which can leave off in the form of HX under the reaction conditions together with the hydrogen atom bonded to the nitrogen atom at 4-position of 1-substituted piperazines or homopiperazines. Examples of the leaving atom or group are halogen atoms, lower alkythio groups (e.g. methylthio, ethylthio, propylthio, butylthio, etc.), arylsulfonyloxy groups (e.g. benzenesulfonyloxy, p-toluenesulfonyloxy, etc.), and alkylsulfonyloxy groups (e.g. methanesulfonyloxy, etc.).

The reaction of the compound of the formula (II) and the compound of the formula (III) is carried out in an appropriate solvent or without using any solvent under atmospheric pressure or under pressure. Suitable examples of the solvent are aromatic hydrocarbons (e.g. toluene, xylene, etc.), ketones (e.g. methyl ethyl ketone, etc.), ethers (e.g. dioxane, diglyme, etc.), alcohols (e.g. ethanol, isopropyl alcohol, butanol, etc.), N,N-dimethylformamide, dimethylsulfoxide. The reaction is preferably carried out in the presence of a basic substance. Suitable examples of the basic substance are alkali metal carbonates (e.g. sodium carbonate, potassium carbonate, etc.), alkali metal hydrogen carbonates (e.g. sodium hydrogen carbonate, potassium hydrogen carbonate, etc.), tertiary amines (e.g. triethylamine, etc.), but an excess amount of the compound of the formula (III) may be used instead of using the basic substance. When the compound of the formula (III) is in the form of a hydrate, the hydrate may be used. The reaction temperature is usually in the range of 40° to 200° C. The starting compound (II) can be prepared in the procedure as described in Reference Examples 1 to 94 hereinafter or in a similar process.

(2) Process B

The compounds of the formula (I) wherein R¹ is a hydrogen atom can be prepared by hydrogenolysis of a compound of the formula (I-4):

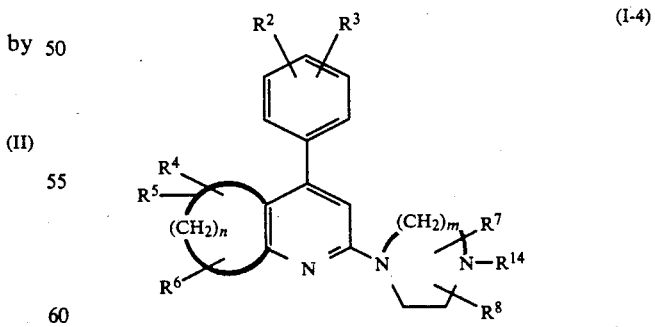

wherein R¹⁴ is unsubstituted or substituted benzyl or benzyloxycarbonyl (the substituent on the phenyl ring of said benzyl and benzyloxycarbonyl is a member selected from lower alkyl, lower alkoxy and halogen atoms), and R², R³, R⁴, R⁵, R⁶, R⁷, R⁸, m and n are as defined above.

The hydrogenolysis of the compounds of the formula (I-4) is usually carried out by a conventional catalytic reduction in a solvent such as alcohols (e.g. ethanol, etc.) at room temperature under atmospheric pressure. The compounds of the formula (I-4) can be prepared by the same process as the above-mentioned Process A. The compounds of the formula (I-4) wherein $R^{14}$ is benzyloxycarbonyl can alternatively be prepared by a conventional process from a compound of the formula (I) wherein $R^{14}$ is methyl or benzyl having optionally a substituent.

(3) Process C

The compounds of the formula (I) wherein $R^1$ is a hydrogen atom can also be prepared by reacting a compound of the formula (I-5):

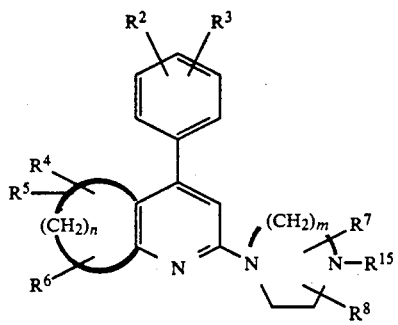

(I-5)

wherein $R^{15}$ is methyl or unsubstituted or substituted benzyl (the substituent on the phenyl ring of the benzyl is a member selected from lower alkyl, lower alkoxy and halogen atoms), and $R^2$, $R^3$, $R^4$, $R^5$, $R^6$, $R^7$, $R^8$, m and n are as defined above, with ethyl chlorocarbonate or 1-chloroethyl chlorocarbonate to give a compound of the formula (I-6):

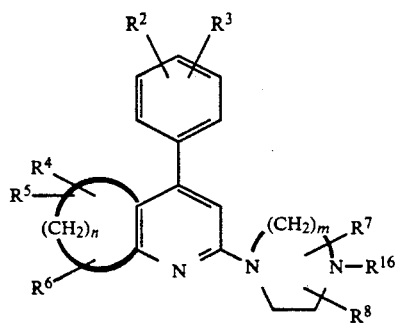

(I-6)

wherein $R^{16}$ is ethoxycarbonyl, 1-chloroethoxycarbonyl, and $R^2$, $R^3$, $R^4$, $R^5$, $R^6$, $R^7$, $R^8$, m and n are as defined above, or a compound of the formula (I-7):

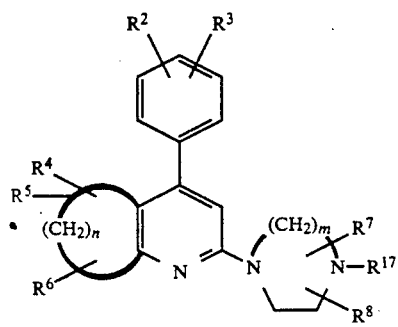

(I-7)

wherein $R^{17}$ is acyl, and $R^2$, $R^3$, $R^4$, $R^5$, $R^6$, $R^7$, $R^8$, m and n are as defined above, followed by hydrolysis of the compound of the formula (I-6) or (I-7).

The hydrolysis of the compound of the formula (I-6) or (I-7) is usually carried out by a conventional method, for example, by heating the compound in an appropriate solvent such as ethanol which is miscible with water in the presence of a basic substance (e.g. sodium hydroxide, potassium hydroxide, etc.) or an acid (e.g. hydrochloric acid, sulfuric acid, etc.). The hydrolysis of the compound of the formula (I-6) wherein $R^{16}$ is 1-chloroethoxycarbonyl is usually carried out by heating the compound in methanol. The compounds of the formulae (I-5) and (I-7) can be prepared by the same process as the above-mentioned Process A.

(4) Process D

The compound of the formula (I) wherein $R^1$ is a group other than a hydrogen atom can be prepared by reacting a compound of the formula (I-8):

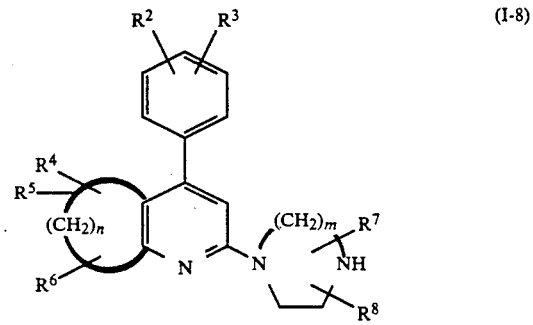

(I-8)

wherein $R^2$, $R^3$, $R^4$, $R^5$, $R^6$, $R^7$, $R^8$, m and n are as defined above, with a compound of the formula (IV):

$$R^{18}-Z \qquad (IV)$$

wherein Z is a reactive residue of an alcohol, and $R^{18}$ is the same as $R^1$ except a hydrogen atom.

The reactive residue of an alcohol represented by the group Z includes, for example, a halogen atom (e.g. chlorine, bromine, iodine, etc.), lower alkylsulfonyloxy (e.g. methanesulfonyloxy, etc.), arylsulfonyloxy (e.g. benzenesulfonyloxy, p-toluenesulfonyloxy, etc.).

The reaction of the compound of the formula (I-8) and the compound of the formula (IV) is usually carried out in an appropriate solvent. Suitable examples of the solvent are aromatic hydrocarbons (e.g. benzene, xylene, etc.), ketones (e.g. methyl ethyl ketone, etc.), ethers (e.g. dioxane, etc.), N,N-dimethylformamide. The reaction is preferably carried out in the presence of a basic substance. The basic substance includes the same substances as used in the above Process A. The reaction temperature is usually in the range of 30° to 150° C. The compounds of the formula (I-8) can be prepared by the same processes as the above-mentioned Processes A to C.

When the compounds of the formula (I) prepared by the Processes A and D have a hydroxyl group in the structure thereof, they can be converted into corresponding ester derivatives or ether derivatives by reacting the compound with an appropriate acylating agent or a lower alkylating agent. These reactions are usually carried out by a conventional method.

The compounds of the formula (I) prepared by the above mentioned Processes can be isolated and purified from the reaction mixture by a conventional method.

The compounds of the formula (I) of the present invention are obtained in the form of a free base or a salt or a hydrate depending on the kinds of the starting compound, the kinds of reaction, the reaction conditions, and the like. When the compounds are obtained in the form of a salt, they can be converted into the corresponding free base by a conventional method, for example, by treating them with a basic substance such as an alkali metal hydroxide. Besides, when the compounds are obtained in the form of a free base, they can be converted into the corresponding salt by a conventional method, for example, by treating them with various acids.

The compounds of the formula (I) of the present invention show inhibitory effect on exploratory activity, antagonistic effect on apomorphine-induced vomiting, binding property to dopamine ($D_2$) and serotonin ($S_2$) receptors, increasing effect on concentration of brain monoamine metabolites, and little toxicity. Accordingly, the compounds of the present invention are useful as an anti-psychotic (neuroleptic) drug or an anti-anxiety (anxiolytic) drug.

Furthermore, the compounds of the formula (I) of the present invention show excellent improving effect in some animal models of memory impairment. Accordingly, the compounds of the present invention are also useful as a medicament for the treatment of various symptoms of cerebral insufficiency.

The compounds of the present invention which show potent antagonistic effect on apomorphine-induced vomiting, binding property to serotonin ($S_2$) and dopamine ($D_2$) receptors, and increasing effect on concentration of brain monoamine metabolites are, for example, the following compounds and a pharmaceutically acceptable salt thereof.

(1) 2-(4-Ethyl-1-piperazinyl)-4-(4-fluorophenyl)-5,6,7,8,9,10-hexahydrocycloocta[b]pyridine
(2) 2-(4-Ethyl-1-piperazinyl)-4-(2,4-difluorophenyl)-5,6,7,8,9,10-hexahydrocycloocta[b]pyridine
(3) 2-(4-Methyl-1-piperazinyl)-4-(4-fluorophenyl)-5,6,7,8,9,10-hexahydrocycloocta[b]pyridine
(4) 2-(4-Methyl-1-piperazinyl)-4-(2,4-difluorophenyl)-5,6,7,8,9,10-hexahydrocycloocta[b]pyridine
(5) 2-(4-n-Propyl-1-piperazinyl)-4-(4-fluorophenyl)-5,6,7,8,9,10-hexahydrocycloocta[b]pyridine
(6) 2-(4-n-Butyl-1-piperazinyl)-4-(4-fluorophenyl)-5,6,7,8,9,10-hexahydrocycloocta[b]pyridine
(7) 2-(4-n-Pentyl-1-piperazinyl)-4-(4-fluorophenyl)-5,6,7,8,9,10-hexahydrocycloocta[b]pyridine
(8) 2-[4-(2-Hydroxyethyl)-1-piperazinyl]-4-(4-fluorophenyl)-5,6,7,8,9,10-hexahydrocycloocta[b]pyridine
(9) 2-(1-Piperazinyl)-4-(4-fluorophenyl)-6,7-dihydro-5H-1-pyrindine
(10) 2-(4-Ethyl-1-piperazinyl)-4-(4-fluorophenyl)-6,7-dihydro-5H-1-pyrindine
(11) 2-[4-(2-Hydroxyethyl)-1-piperazinyl]-4-(4-fluorophenyl)-6,7-dihydro-5H-1-pyrindine
(12) 2-(4-Ethyl-1-piperazinyl)-4-phenyl-6,7,8,9-tetrahydro-5H-cyclohepta[b]pyridine
(13) 2-(4-Ethyl-1-piperazinyl)-4-(4-fluorophenyl)-6,7,8,9-tetrahydro-5H-cyclohepta[b]pyridine
(14) 2-(4-Ethyl-1-piperazinyl)-4-(4-fluorophenyl)-5,6,7,8-tetrahydroquinoline-5,8-methanoquinoline
(15) 2-(4-Ethyl-1-piperazinyl)-4-(2,4-difluorophenyl)-5,6,7,8-tetrahydro-5,8-methanoquinoline
(16) 2-(4-Ethyl-1-piperazinyl)-4-(4-fluorophenyl)-6,7,8,9-tetrahydro-5H-6,9-methanocyclohepta[b]pyridine
(17) 2-(4-Ethyl-1-piperazinyl)-4-(4-fluoro-phenyl)-6,7,8,9-tetrahydro-5H-5,8-methanocyclohepta[b]pyridine The compounds of the present invention which have excellent improving effects on behavioral and/or memory deficites induced by scopolamine or cycloheximide are, for example, the following compounds and a pharmaceutically acceptable salt thereof.

(1) 2-(1-Piperazinyl)-4-phenyl-6,7-dihydro-5H-1-pyrindine
(2) 2-(1-Piperazinyl)-4-(4-fluorophenyl)-6,7-dihydro-5H-1-pyrindine
(3) 2-(1-Piperazinyl)-4-phenyl-5,6,7,8-tetrahydroquinoline
(4) 2-(1-Piperazinyl)-4-(4-fluorophenyl)-5,6,7,8-tetrahydroquinoline
(5) 2-(1-Piperazinyl)-4-(4-fluorophenyl)-6,7,8,9-tetrahydro-5H-cyclohepta[b]pyridine The pharmacological activities of the representative compounds of the present invention are illustrated by the following Experiments.

In the Experiments, the following compounds, which are disclosed in the above mentioned U.S. Pat. No. 4,469,696, were used as reference.

Test Compound A (disclosed in Example 4):
4,5-Bis-(4-fluorophenyl)-6-methyl-2-(4-phenylpiperazino)pyridine Test Compound B (disclosed in Example 1):
4,5-Bis-(4-methoxyphenyl)-6-methyl-2-(4-phenylpiperazino)pyridine Test Compound C (disclosed in Example 2):
4,5-Bis-(4-hydroxyphenyl)-6-methyl-2-(4-phenylpiperazino)pyridine

EXPERIMENT 1

Inhibitory Effect on Exploratory Activity

A group of 5 male mice (Std-ddy strain, 20–25 g) was used. Two hours after oral administration of the test compound, mice were placed individually in a test box (23×35×30 cm) on Animex activity meter (Farad Co.). Immediately thereafter, activity counting was started and lasted for three minutes. The mean counts of the compound-treated group were compared with those of the corresponding control (non-dosed) group, and the percent inhibition was calculated. The results are shown in Table 1.

TABLE 1

| Inhibitory effect on exploratory activity | | | |
|---|---|---|---|
| Test compound | Inhibitory ratio (%) | Test compound | Inhibitory ratio (%) |
| Ex. | | | |
| 1b* | 83.7 | 83 | 53.5 |
| 2a | 77.5 | 106 | 74.9 |
| 31 | 62.5 | 107 | 53.2 |
| 36 | 68.4 | 111 | 74.0 |
| 38 | 58.9 | 112 | 73.2 |
| 53 | 68.1 | 114 | 81.9 |
| 57 | 77.2 | 122 | 81.3 |
| 71 | 61.9 | 123 | 72.2 |
| 75 | 78.9 | 125 | 57.9 |
| 76 | 87.6 | 127 | 80.3 |

*The compound of Example 1b (hereinafter, the same)

EXPERIMENT 2

Antagonistic Effect on Apomorphine-induced Vomiting:

A group of 3-4 dogs (Beagle, 8-15 kg) was used for examining effects on the test compounds on apomorphine-induced vomiting, a known test for evaluating neuroleptic drugs.

Each dog was given a subcutaneous injection of apomorphine hydrochloride (0.3 mg/kg) two hours after the treatment of the test compounds. Then, the frequency of oral vomiting was counted for one hour. The mean counts of the compound-treated group were compared with those of the corresponding control (non-dosed) group, and the percent inhibition was calculated. The results are shown in Table 2.

TABLE 2

Antagonistic effect on apomorphine-induced vomiting

| Test comp. | Dose (mg/kg) | Inhibitory ratio (%) | Test comp. | Dose (mg/kg) | Inhibitory ratio (%) |
|---|---|---|---|---|---|
| Ex. | | | Ex. | | |
| 1a[1] | 0.2 | 100 | 73 | 1.0 | 100 |
| 1b | 0.3 | 88 | 76 | 0.3 | 71 |
| 2b | 0.2 | 100 | 77 | 0.5 | 61 |
| 6 | 1.0 | 89 | 82 | 1.0 | 100 |
| 7 | 1.0 | 80 | 88 | 3.0 | 94 |
| 15 | 3.0 | 100 | 112 | 0.2 | 94 |
| 25 | 3.0 | 100 | 114 | 0.2 | 89 |
| 27 | 3.0 | 47 | 116 | 1.0 | 100 |
| 29 | 3.0 | 63 | 118 | 0.3 | 94 |
| 36 | 0.5 | 81 | 121 | 0.5 | 93 |
| 37 | 0.3 | 80 | 122 | 0.5 | 100 |
| 43 | 1.0 | 96 | 135 | 1.0 | 100 |
| 56 | 0.5 | 85 | A[2] | 3.0 | 11 |
| 66 | 1.0 | 95 | B[2] | 3.0 | 13 |
| 71 | 3.0 | 84 | C[2] | 3.0 | 16 |

[1]The compound of Example 1a (hereinafter, the same)
[2]The compounds disclosed in the U.S. Pat. No. 4,469,696

EXPERIMENT 3

In Vitro Binding Property to Dopamine ($D_2$), Serotonin ($S_1$, $S_2$) and Adrenaline ($\alpha_1$) Receptors:

Dopamine ($D_2$), serotonin ($S_1$, $S_2$) and adrenaline ($\alpha_1$) receptor binding assays were carried out according to the methods of I. Creese et al. [Eur. J. Pharmacol., 46, 377 (1977), S. J. Peroutka et al. [Mol. Pharmacol. 16, 687 (1979)], J. E. Leysen et al. [Mol. Pharmacol., 21, 301 (1982)] and D. C. U'Prichard et al. [Mol. Pharmacol., 13, 454 (1977)], respectively.

Crude synaptosome fractions were prepared from some brain regions in rats for receptor sources. Radioactive ligands used were [$^3$H] spiperone ($D_2$), [$^3$H] serotonin ($S_1$), [$^3$H] ketanserin ($S_2$) and [$^3$H] WB-4101 ($\alpha_1$). The binding assay was performed by incubating aliquots of synaptosome fraction in buffer solution (final volume: 1 ml) containing a [$^3$H] labelled ligand and a test compound. The assay was terminated by rapid filtration through Whatman GF/B glass fiber filters attached to a cell-harvester (Brandel) and radioactivity on the filters was counted in a Packard Triscarb scintillation counter. Specific binding was calculated as a difference between amounts of radioactivity in the presence and absence of an unlabelled ligand [spiperone ($D_2$), serotonin ($S_1$), methysergide ($S_2$) and prazosin ($\alpha_1$)]. The $IC_{50}$ value of the test compounds (concentration causing 50% inhibition of [$^3$H] ligand specific binding) was determined by probit analysis. The results are shown in Table 3.

TABLE 3

Binding property to dopamine ($D_2$), sertonin ($S_1$, $S_2$) and adrenaline ($\alpha_1$) receptor

| Test compound | $IC_{50}$ (nM) | | | |
|---|---|---|---|---|
| | $D_2$ | $S_1$ | $S_2$ | $\alpha_1$ |
| Ex. | | | | |
| 1a[1] | 24 | — | 9.9 | 83 |
| 1b | 46 | — | 7.0 | 92 |
| 2a | 24 | — | 28 | 88 |
| 6 | 19 | 1500 | 7.6 | 6.9 |
| 7 | 30 | — | 9.5 | — |
| 15 | 58 | 1700 | 19 | 35 |
| 23 | 96 | 2900 | 7.7 | 320 |
| 25 | 77 | 2600 | 2.3 | 120 |
| 71 | 25 | — | 14 | 13 |
| 73 | 18 | — | 2.4 | 4.6 |
| 86 | 730 | 1400 | 81 | 530 |
| 87 | 270 | 820 | 28 | 94 |
| 88 | 70 | 670 | 9.1 | 65 |
| 92 | 300 | 1900 | 27 | 380 |
| 96 | 660 | 4900 | 62 | 1100 |
| 97 | 260 | 4100 | 5.1 | 890 |
| 103 | 140 | — | 41 | — |
| A[2] | >10000 | — | >10000 | >10000 |
| B[2] | >10000 | — | — | — |
| C[2] | >10000 | — | — | — |

[1]The compound of Example 1a (hereinafter, the same)
[2]The compounds disclosed in the U.S. Pat. No. 4,469,696

EXPERIMENT 4

Increasing Effect on Concentration of Brain Monoamine Metabolites

A group of 5 male mice (Std-ddy strain, 25-30 g) was used for examining effect of the test compounds on concentration of brain monoamine metabolites. It is generally accepted that an increase in each monoamine is mainly caused by each monoamine receptor blockade.

Mice were killed by decapitation 2 hours after treatment with the test compounds. Brains were quickly taken out, homogenized in 1N formic acid-acetone solution, and centrifuged in a refrigerated ultracentrifuge. The supernatant was evaporated by blowing with $N_2$ gas. Then, the residue was again resolved in 0.01 N acetic acid, and served for determining concentration of dopamine metabolites, 3,4-dihydroxyphenylacetic acid (DOPAC) and homovanillic acid (HVA), a norepinephrine metabolite, 3-methyl-4-hydroxyphenylethylene glycol (MOPEG), and a serotonin metabolite, 5-hydroxyindole-3-acetic acid (5-HIAA) concentrations by HPLC with electrochemical detection. The effect of the test compounds on concentration of each monoamine metabolite is shown as % of control (level of non-dosed animals=100) in Table 4.

TABLE 4

Increasing effect on the concentration of monoamine metabolites

| Test compound | Dose (mg/kg) | DOPAC (%) | HVA | MOPEG | 5-HIAA |
|---|---|---|---|---|---|
| EX. | | | | | |
| 1b* | 1 | 235 | 212 | 118 | 102 |
| 2b | 2 | 364 | 271 | — | — |
| 6 | 10 | 321 | 242 | 115 | 103 |
| 15 | 10 | 277 | 235 | 118 | 108 |
| 23 | 10 | 344 | 320 | 115 | 145 |
| 24 | 10 | 290 | 317 | 139 | 150 |
| 25 | 1 | 272 | 207 | 106 | 113 |
| 26 | 10 | 344 | 263 | — | — |
| 27 | 10 | 208 | 193 | — | — |

TABLE 4-continued

Increasing effect on the concentration of monoamine metabolites

| Test compound | Dose (mg/kg) | DOPAC | (%) HVA | MOPEG | 5-HIAA |
|---|---|---|---|---|---|
| 29 | 10 | 296 | 274 | — | — |
| 35 | 10 | 165 | 170 | — | — |
| 37 | 3 | 268 | 203 | 143 | 95 |
| 39 | 10 | 307 | 233 | 117 | 97 |
| 42 | 10 | 258 | 211 | — | — |
| 44 | 10 | 272 | 210 | — | — |
| 46 | 10 | 296 | 235 | — | — |
| 49 | 10 | 197 | 195 | — | — |
| 52 | 10 | 233 | 216 | — | — |
| 54 | 2 | 251 | 250 | — | — |
| 55 | 2 | 379 | 240 | — | — |
| 56 | 10 | 302 | 249 | 106 | 110 |
| 59 | 2 | 246 | 236 | 126 | 106 |
| 66 | 2 | 311 | 308 | 111 | 116 |
| 68 | 2 | 206 | 181 | — | — |
| 84 | 10 | 237 | 216 | — | — |
| 87 | 10 | 180 | 194 | 117 | 136 |
| 88 | 10 | 329 | 209 | 136 | 120 |
| 92 | 10 | 208 | 192 | 121 | 139 |
| 96 | 10 | 201 | 194 | 115 | 127 |
| 97 | 10 | 232 | 176 | 125 | 128 |
| 104 | 10 | 344 | 247 | 160 | 97 |
| 117 | 10 | 242 | 210 | 133 | 100 |
| 118 | 3 | 302 | 250 | 129 | 110 |
| 121 | 10 | 312 | 215 | — | 111 |
| 122 | 2 | 306 | 229 | — | 100 |
| 124 | 10 | 292 | 238 | 102 | 107 |
| 131 | 1 | 319 | 224 | — | — |
| 132 | 10 | 333 | 209 | — | — |
| 138 | 2 | 236 | 173 | — | — |
| 139 | 10 | 267 | 206 | — | — |

*The compound of Example 1b (hereinafter, the same)

EXPERIMENT 5

Improving Effect on Scopolamine-induced Deficit of Spontaneous Alternation Behavior A group of 15-25 male mice (Std-ddY strain, 22-28 g) was used for evaluating effect of the test compounds on scopolamine-induced deficit of spontaneous alternation in a T-maze, which is a known animal model of memory impairment due to hypofunction of the cholinergic nervous system. The T-maze used consists of a stem and two arms which are 25 cm long, 5 cm wide and 10 cm high. The first 10 cm of the stem and last 10 cm of each arm are divided by sliding doors into start and goal boxes.

A test compound and scopolamine hydrobromide (1 mg/kg) were intraperitoneally administered to each mouse, and after 30 minutes a test of spontaneous alternation task in the T-maze was continuously repeated for 8 trials. Commonly, naive mice alternate each (right and left) goal box in turn, but scopolamine-treated animals tend to enter the same goal box repeatedly. The effect of the test compounds was expressed as % improvement (complete improvement to the alternation level of non-dosed mice=100%). The results are shown in Table 5.

TABLE 5

Improving effect on scopolamine-induced deficit of spontaneous alternation behavior

| Test compound | Dose (mg/kg) | Improvement (%) |
|---|---|---|
| Ex. | | |
| 86* | 10.0 | 47.6 |
| 87 | 0.5 | 48.0 |
| | 2.0 | 60.0 |
| 88 | 10.0 | 37.0 |
| 97 | 10.0 | 32.0 |

*The compound of Example 86 (hereinafter the same)

EXPERIMENT 6

Improving Effect on Cycloheximide-induced Amnesia of Passive Avoidance Response

Anti-amnesic effect of the test compounds was examined using mice given cycloheximide, which is a known amnesia-inducing agent.

A group of 15-20 male mice (Std-ddY strain, 27-33 g) was subjected to training and retention trials for a passive avoidance task in a step-down apparatus (30×30×50 cm) with a grid floor and a wooden platform (4×4×4 cm) in a center of the floor. In the training trial, each mouse was first placed on the platform. When the mouse stepped down on the grid floor, an electric shock (1 Hz, 0.5 sec, 60 VDC) was delivered to the feet for 15 seconds. Immediately after the training trial, cycloheximide (60 mg/kg, s.c.) and a test compound (i.p.) were administered. The retention trial was carried out 24 hours thereafter, the time from placing again each mouse placed on the platform until stepping down on the grid floor (step-down latency) was measured. The step-down latency in the retention trial was markedly shortened by treatment of cycloheximide (amnesia). The effect of test compounds was assessed by % improvement (complete improvement to the latency level of non-dosed animals=100%). The results are shown in Table 6.

TABLE 6

Improving effect on cycloheximide-induced amnesia of passive avoidance response

| Test compound | Dose (mg/kg) | Improvement (%) |
|---|---|---|
| Ex. | | |
| 87* | 0.5 | 48 |
| | 2.0 | 77 |
| 88 | 2.0 | 60 |
| 92 | 2.0 | 44 |
| | 10.0 | 78 |
| 96 | 0.5 | 81 |
| | 2.0 | 64 |
| 97 | 0.5 | 38 |
| | 2.0 | 36 |

*The compound of Example 87 (hereinafter the same)

EXPERIMENT 7

Acute Toxicity

A group of 5 male mice (Std-ddy strain, 25-30 g) was used. The test compound was orally administered to the test animal in the form of a 0.5% tragacanth solution or suspension, and for 7 days after the administration of the test compound, the lethality of animals was observed. The results are shown in Table 7.

TABLE 7

Acute toxicity

| Test compound | Dose (mg/kg) | Number of dead animals Number of test animals |
|---|---|---|
| Ex. | | |
| 1a* | 500 | 0/5 |

TABLE 7-continued

| Test compound | Acute toxicity | |
|---|---|---|
| | Dose (mg/kg) | Number of dead animals / Number of test animals |
| 1b | 500 | 0/5 |
| 2b | 500 | 0/5 |
| 6 | 500 | 0/5 |
| 25 | 500 | 0/5 |
| 76 | 500 | 0/5 |

*The compound of Example 1a (hereinafter, the same)

The compounds of the present invention can be administered either in oral route, parenteral route or intrarectal route, but preferably in oral route. The dose of the compounds may vary depending on the kinds of the compounds, administration routes, severity of the disease and age of patients, but is usually in the range of 0.01 to 50 mg/kg/day, preferably 0.01 to 5 mg/kg/day.

The compounds of the present invention are usually administered in the form of a conventional pharmaceutical preparation in admixture with a conventional pharmaceutically acceptable carrier or diluent. The pharmaceutically acceptable carrier or diluent includes the conventional pharmaceutically acceptable carriers or diluents which do not react with the compounds of the present invention. Suitable examples of the carrier or diluent are lactose, glucose, mannitol, sorbitol, dextrin, cyclodextrin, starch, sucrose, magnesium metasilicate aluminate, synthetic aluminum silicate, crystalline cellulose, sodium carboxymethyl cellulose, hydroxypropyl starch, calcium carboxymethyl cellulose, ion exchange resin, methyl cellulose, gelatin, acacia, pullulan, hydroxypropyl cellulose, low substituted hydroxypropyl cellulose, hydroxypropyl methyl cellulose, polyvinylpyrrolidone, polyvinyl alcohol, light silicic anhydride, magnesium stearate, talc, tragacanth, bentonite, veegum, carboxyvinyl polymer, titanium oxide, sorbitan fatty acid ester, sodium laurylsulfate, glycerin, glycerin fatty acid ester, anhydrous lanolin, glycerogelatin, polysorbate, macrogol, vegetable oil, wax, propylene glycol, water, and the like. The pharmaceutical preparation includes tablets, capsules, granules, fine granules, powders, syrups, suspensions, injections, suppositories, and the like. These preparations can be prepared by a conventional method. The liquid preparations may be in the form that they are dissolved or suspended in water or any other conventional medium when used. The tablets, granules and fine granules may be coated with a conventional coating agent. The injections are usually prepared by dissolving the compound of the present invention in water, but occasionally in a physiological saline solution or glucose solution, which is optionally incorporated with a buffer or a preservative. The pharmaceutical preparations may also contain other pharmaceutically active compounds.

The present invention is illustrated by the following Reference Examples, Examples and Preparations, but should not be construed to be limited thereto. The compounds are identified by elementary analysis, mass spectrum, IR spectrum, UV spectrum, NMR spectrum, and the like.

In the Reference Examples and Examples, the following abbreviations may occasionally be used.
Me: methyl
Et: ethyl
t-Bu: tertiary butyl
Ph: phenyl
A: ethanol
AC: acetonitrile
AT: acetone
CF: chloroform
D: N,N-dimethylformamide
E: diethyl ether
EA: ethyl acetate
HX: hexane
IP: isopropyl alcohol
M: methanol
MC: methylene chloride
PE: petroleum ether
T: toluene
W: water Besides, the solvent shown in brackets as to the melting point in the following Reference Examples and Examples means a solvent for recrystallization.

REFERENCE EXAMPLE 1

Preparation of 4-phenyl-5,6,7,8-tetrahydro-2(1H)-quinolinone

A mixture of benzoylacetonitrile (25 g), cyclohexanone (25 g) and 75% polyphosphoric acid (250 g) is stirred at 50° C. for 30 minutes and further at 110° C. for 1.5 hour. After cooling, the reaction mixture is poured into ice-water and thereto is added diethyl ether (300 ml). The mixture is stirred and the precipitated crystals are collected by filtration. The crystals are recrystallized from N,N-dimethylformamide-ethanol to give the desired compound (27 g), m.p. 285°–288° C.

REFERENCE EXAMPLES 2 TO 46

In the same manner as described in Reference Example 1 except that the corresponding starting materials are used, there are obtained the compounds as shown in the following Tables 8 and 9.

TABLE 8

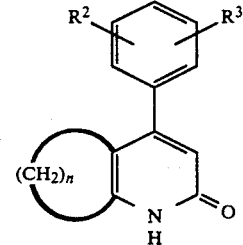

| Ref. Ex. | n | $R^2$ | $R^3$ | Melting point (°C.) | Solvent for recrystallization |
|---|---|---|---|---|---|
| 2 | 3 | H | H | 221–223 | M |
| 3 | 3 | 4-F | H | 258–265 | M |
| 4 | 3 | 3-F | H | 234–235 | A |
| 5 | 3 | 2-F | H | 210–212 | A-W |
| 6 | 3 | 4-OMe | H | 243–245 | M |
| 7 | 3 | 4-F | 2-F | 235–245 | A |
| 8 | 4 | 4-F | H | 287–288 | D-A |
| 9 | 4 | 3-F | H | 253–255 | A |
| 10 | 4 | 2-F | H | 174–176 | M |
| 11 | 4 | 4-OMe | H | 239–242 | M |
| 12 | 5 | H | H | 280–281 | M |
| 13 | 5 | 4-F | H | 245–246 | M |
| 14 | 5 | 3-F | H | 273–275 | M |
| 15 | 5 | 2-F | H | 251–252 | A-W |
| 16 | 5 | 4-OMe | H | 258–260 | M |
| 17 | 5 | 2-OMe | H | 245–247 | A |
| 18 | 5 | 4-Me | H | 253–258 | M |
| 19 | 5 | 4-Cl | H | 251–255 | D-W |
| 20 | 5 | 2-Cl | H | 262–263 | D-W |
| 21 | 5 | 4-F | 2-F | 233–235 | A |
| 22 | 6 | H | H | 265–266 | M |
| 23 | 6 | 4-F | H | 235–238 | IP |

TABLE 8-continued

| Ref. Ex. | n | R² | R³ | Melting point (°C.) | Solvent for recrystallization |
|---|---|---|---|---|---|
| 24 | 6 | 3-F | H | 260–270 | A |
| 25 | 6 | 2-F | H | 245–247 | IP |
| 26 | 6 | 4-F | 3-F | 255–261 | M |
| 27 | 6 | 4-F | 2-F | 240–243 | M |
| 28 | 6 | 6-F | 2-F | 254–256 | A |
| 29 | 6 | 4-OMe | H | 267–271 | M |
| 30 | 6 | 4-Me | H | 265–275 | A |
| 31 | 6 | 4-Cl | H | 284–287 | M |
| 32 | 6 | 3-Cl | H | 248–250 | A |
| 33 | 6 | 4-Br | H | 286–292 | M |
| 34 | 7 | 4-F | H | 241–243 | EA |

TABLE 9

| Ref. Ex. | W/Y group | R³ | R³ | Melting point (°C.) | Solvent for recrystallization |
|---|---|---|---|---|---|
| 35 | Me-cyclohexenyl (Me) | H | H | 275–279 | M |
| 36 | Me-cyclohexenyl (Me) | F | H | 270–275 | M |
| 37 | cyclohexenyl-Me | F | H | 255–257 | M |
| 38 | Me,Me-cyclohexenyl (Me) | F | H | 278–284 | M |
| 39 | Me-cyclohexenyl (Me, Me,Me) | F | H | 266–267 | M |
| 40 | Me-cyclohexenyl (Me, CHMe₂) | F | H | — | — |
| 41 | t-Bu-cyclohexenyl | H | H | 272–276 | M |
| 42 | Ph-cyclohexenyl | F | H | 273–277 | M |
| 43 | norbornenyl | H | H | 220–225 | IP |
| 44 | norbornenyl | F | H | 263–274 | A |
| 45 | norbornenyl | F | F | — | — |
| 46 | bicyclic | F | H | >300 | M |

REFERENCE EXAMPLE 47

Preparation of 4-(4-fluorophenyl)-1,5,6,7,8,9-hexahydro-2H-6,9-methanocyclohepta[b]pyridin-2-one Bicyclo[3.2.1]octan-2-one (2 g) and 4-fluorobenzoylacetonitrile (2.6 g) are dissolved in 1,1,2,2-tetrachloroethane (5 ml) and thereto is added 75% polyphosphoric acid (25 g). The mixture is stirred at 80° C. for 30 minutes, at 100° C. for 1 hour, and further at 130° C. for 30 minutes. After cooling, the reaction mixture is poured into ice-water and neutralized with potassium carbonate. The precipitated crystals are collected by filtration and washed successively with water and ethyl acetate. The resultant is recrystallized from methanol to give the desired product (2.7 g), m.p.>300° C.

REFERENCE EXAMPLE 48

Preparation of 4-(4-fluorophenyl)-1,5,6,7,8,9-hexahydro-2H-5,8-methanocyclohepta[b]pyridin-2-one In the same manner as described in Reference Example 47 except that the corresponding starting materials are used, there is obtained the desired compound.

REFERENCE EXAMPLE 49

Preparation of 2-chloro-4-(4-fluorophenyl)-5,6,7,8-tetrahydroquinoline:

A mixture of 4-(4-fluorophenyl)-5,6,7,8-tetrahydro-2(1H)-quinoline (18.7 g) and phenylphosphonic dichloride (29 ml) is stirred at 170° C. for 1 hour. After cooling, the reaction mixture is dissolved in chloroform (200 ml) and the mixture is added dropwise into ice-water with stirring over a period of about 30 minutes. The mixture is made alkaline by dropwise addition of conc. aqueous ammonia thereto. The organic layer is separated, washed with water, dried over anhydrous sodium sulfate, and concentrated under reduced pressure. The residue is recrystallized from isopropanol-petroleum ether to give the desired product (15.1 g), m.p. 111°–112° C.

REFERENCE EXAMPLES 50 TO 94

In the same manner as described in Reference Example 49 except that the corresponding starting materials are used, there are obtained the compounds as shown in Table 10 and 11.

TABLE 10

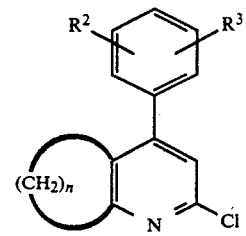

| Ref. Ex. | n | $R^2$ | $R^3$ | Melting point (°C.) | Solvent for recrystallization |
|---|---|---|---|---|---|
| 50 | 3 | H | H | 86–87 | IP-PE |
| 51 | 3 | 4-F | H | 144–146 | A |
| 52 | 3 | 3-F | H | 55–57 | IP |
| 53 | 3 | 2-F | H | Oil | — |
| 54 | 3 | 4-OMe | H | Oil | — |
| 55 | 3 | 4-F | 2-F | Oil | — |
| 56 | 4 | H | H | 86–88 | A |
| 57 | 4 | 3-F | H | 84–86 | A |
| 58 | 4 | 2-F | H | 84–85 | IP-PE |
| 59 | 4 | 4-OMe | H | 104–106 | A |
| 60 | 5 | H | H | 71–72 | IP |
| 61 | 5 | 4-F | H | 84–85 | PE |
| 62 | 5 | 3-F | H | Oil | — |
| 63 | 5 | 2-F | H | 89–90 | A |
| 64 | 5 | 4-OMe | H | 75–76 | A |
| 65 | 5 | 4-Me | H | 66–67 | A |
| 66 | 5 | 4-Cl | H | 117–118 | MC-HX |
| 67 | 5 | 4-F | 2-F | 55–56 | IP |
| 68 | 6 | H | H | 96–97 | IP-PE |
| 69 | 6 | 4-F | H | 136–137 | A |
| 70 | 6 | 3-F | H | 110–111 | A |
| 71 | 6 | 2-F | H | 81–82 | IP |
| 72 | 6 | 4-F | 3-F | 137–138 | A |
| 73 | 6 | 4-F | 2-F | 74–75 | IP |
| 74 | 6 | 6-F | 2-F | 83–84 | IP |
| 75 | 6 | 4-OMe | H | 147–150 | MC-HX |
| 76 | 6 | 4-Me | H | 142–143 | M |
| 77 | 6 | 4-Cl | H | 183–185 | CF-T |
| 78 | 6 | 3-Cl | H | 100–101 | A |
| 79 | 6 | 4-Br | H | Oil | — |
| 80 | 7 | 4-F | H | 60–68 | E |

TABLE 11

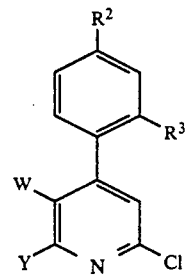

| Ref. Ex. | W–Y group | $R^2$ | $R^3$ | Melting point (°C.) | Solvent for recrystallization |
|---|---|---|---|---|---|
| 81 | 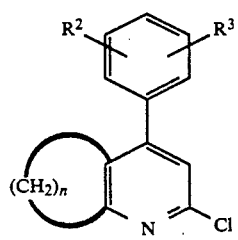 | H | H | 94–95 | IP |
| 82 | Me-cyclohexene | F | H | 94–95 | A |
| 83 | Me-cyclohexyl-Me | F | H | 74–75 | IP |

TABLE 11-continued

[Structure: pyridine with R² and R³ on phenyl ring at position 4, W and Y substituents, Cl at position 2]

| Ref. Ex. | W/Y (structure) | R² | R³ | Melting point (°C.) | Solvent for recrystallization |
|---|---|---|---|---|---|
| 84 | Me, Me-cyclohexenyl with dimethyl | F | H | 102–104 | MC-HX |
| 85 | t-Bu-cyclohexenyl with dimethyl | H | H | 109–110 | A |
| 86 | Ph-cyclohexenyl with dimethyl | F | H | 159–162 | CF-A |
| 87 | Me-cyclohexenyl with Me, Me | F | H | 83–84 | IP |
| 88 | Me-cyclohexenyl with Me, CH(Me)Me | F | H | — | — |
| 89 | norbornenyl dimethyl | H | H | 63–65 | IP-PE |
| 90 | norbornenyl dimethyl | F | H | 74–76 | IP |
| 91 | norbornenyl dimethyl | F | F | Oil | — |
| 92 | bicyclic dimethyl | F | H | 132–135 | MC-HX |
| 93 | bicyclooctenyl dimethyl | H | H | Oil | — |
| 94 | bicyclooctenyl dimethyl | F | H | 92–94 | MC-HX |

EXAMPLE 1

Preparation of 2-(4-ethyl-1-piperazinyl)-4-(4-fluorophenyl)-5,6,7,8,9,10-hexahydrocycloocta[b]pyridine A mixture of 2-chloro-4-(4-fluorophenyl)-5,6,7,8,9,10-hexahydrocycloocta[b]pyridine (2.0 g), N-ethylpiperazine (2.4 g), and potassium iodide (1.1 g) is stirred at 170° C. for 5 hours. After cooling, the reaction mixture is dissolved in ethyl acetate and water. The organic layer is washed with water and extracted with 5% hydrochloric acid. The extract is made alkaline with potassium carbonate, and extracted with ethyl acetate. The extract is washed with water, dried over anhydrous sodium sulfate, and concentrated under reduced pressure.

(a) The residue is recrystallized from acetonitrile to give the desired product (1.2 g), m.p. 123°–124° C.

This product obtained in the above (a) is converted to the following salt thereof by treating the product with various acids.

(b) Dimaleate, m.p. 165°–167° C. (ethanol)
(c) Dihydrochloride·½ hydrate, m.p. 215°–222° C. (acetone)
(d) Fumarate, m.p. 228°–230° C. (ethanol)
(e) Citrate, m.p. 184°–187° C. (ethanol)

EXAMPLE 2

Preparation of 2-(4-ethyl-1-piperazinyl)-4-(2,4-difluorophenyl)-5,6,7,8,9,10-hexahydrocycloocta[b] pyridine A mixture of 2-chloro-4-(2,4-difluorophenyl)-5,6,7,8,9,10-hexahydrocycloocta[b]pyridine (10 g), N-ethylpiperazine (11 g), and potassium iodide (5.4 g) is stirred at 170° C. for 5 hours. After cooling, the reaction mixture is dissolved in chloroform and 5% aqueous potassium carbonate solution. The organic layer is washed with water, dried over anhydrous sodium sulfate, and concentrated under reduced pressure.

(a) The residue is dissolved in toluene, and subjected to silica gel column chromatography. The fractions eluted with toluene and a mixture of toluene-ethyl acetate (1:1) are collected, and recrystallized from isopropyl alcohol to give the desired product (5.5 g), m.p. 124°–125° C.

(b) The product obtained in the above (a) is treated with a solution of maleic acid in ethanol to give the dimaleate of the desired product, m.p. 133°–135° C. (ethanol).

EXAMPLE 3

Preparation of 2-(4-ethyl-1-piperazinyl)-4-phenyl-5,6,7,8-tetarahydroquinoline

A mixture of 2-chloro-4-phenyl-5,6,7,8-tetrahydroquinoline (1.0 g), N-ethylpiperazine (1.2 g), and potassium iodide (0.66 g) is stirred at 170° C. for 15 hours. After cooling, the reaction mixture is dissolved in chloroform, and 5% aqueous potassium carbonate solution. The organic layer is washed with water, dried over anhydrous sodium sulfate, and concentrated under reduced pressure. The resulting oily residue is subjected to basic alumina column chromatography. The fractions eluted with toluene and a mixture of toluene and ethyl acetate (9:1) are collected, and treated with a solution of maleic acid in ethanol. The resulting maleate product is recrystallized from ethanolethyl acetate to give the dimaleate of the desired product (0.45 g), m.p. 139°–142° C.

EXAMPLES 4–77

In the same manner as described in Example 3 except that the corresponding starting materials are used, there are obtained the compounds as shown in Tables 12 and 13.

TABLE 12

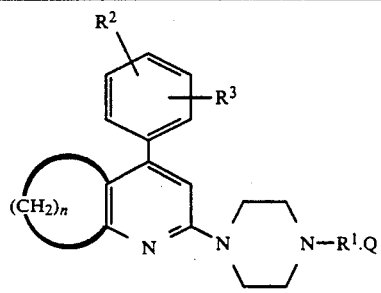

| Ex. | n | $R^2$ | $R^3$ | $R^1$ | Q | M.p. (°C.) | Sol. recry. |
|---|---|---|---|---|---|---|---|
| 4 | 3 | H | H | Et | 3/2 Maleate | 132–136 | A |
| 5 | 3 | H | H | $CH_2CH_2OH$ | Maleate | 178–183 | A |
| 6 | 3 | 4-F | H | Et | Dimaleate | 164–166 | A |
| 7 | 3 | 4-F | H | $CH_2CH_2OH$ | ½ Fumarate | 207–210 | M |
| 8 | 3 | 3-F | H | Et | Dimaleate | 124–126 | A |
| 9 | 3 | 3-F | H | $CH_2CH_2OH$ | Maleate.¼ $H_2O$ | 182–185 | A |
| 10 | 3 | 2-F | H | Et | Maleate.1/5 $H_2O$ | 189–191 | A |
| 11 | 3 | 2-F | H | $CH_2CH_2OH$ | Maleate.¼ $H_2O$ | 186–188 | A |
| 12 | 3 | 4-OMe | H | Et | Dimaleate | 174–176 | A |
| 13 | 3 | 4-OMe | H | $CH_2CH_2OH$ | Dioxalate | 183–187 | M |
| 14 | 4 | H | H | $CH_2CH_2OH$ | Dimaleate | 129–131 | A |
| 15 | 4 | 4-F | H | Et | Dimaleate | 146–148 | A |
| 16 | 4 | 4-F | H | $CH_2CH_2OH$ | Dimaleate | 149–151 | A |
| 17 | 4 | 3-F | H | Et | Dimaleate | 133–136 | M |
| 18 | 4 | 3-F | H | $CH_2CH_2OH$ | Dioxalate | 180–182 | M |
| 19 | 4 | 2-F | H | Et | Dimaleate | 148–150 | A |
| 20 | 4 | 2-F | H | $CH_2CH_2OH$ | Dioxalate.¼ $H_2O$ | 169–172 | A |
| 21 | 4 | 4-OMe | H | Et | Dimaleate | 179–181 | A |
| 22 | 4 | 4-OMe | H | $CH_2CH_2OH$ | Dioxalate.¼ $H_2O$ | 160–165 | A |
| 23 | 5 | H | H | Et | Dimaleate | 150–152 | IP |
| 24 | 5 | H | H | $CH_2CH_2OH$ | ½ Fumarate | 142–144 | A |
| 25 | 5 | 4-F | H | Et | Dimaleate | 150–152 | A |
| 26 | 5 | 4-F | H | $CH_2CH_2OH$ | 1.7 Oxalate | 180–182 | A |
| 27 | 5 | 3-F | H | Et | Dimaleate | 138–140 | A |
| 28 | 5 | 3-F | H | $CH_2CH_2OH$ | Maleate.¼ $H_2O$ | 155–158 | IP |
| 29 | 5 | 2-F | H | Et | Oxalate | 231–234 | A-M |
| 30 | 5 | 2-F | H | $CH_2CH_2OH$ | ½ Fumarate.¼ $H_2O$ | 163–164 | M |
| 31 | 5 | 4-Cl | H | Et | — | 150–151 | MC-A |
| 32 | 5 | 4-OMe | H | Et | Dimaleate | 162–164 | A |
| 33 | 5 | 4-OMe | H | $CH_2CH_2OH$ | Fumarate.¼ $H_2O$ | 190–195 | A-M |
| 34 | 5 | 4-Me | H | Et | Dimaleate | 180–183 | A |
| 35 | 5 | 4-Me | H | $CH_2CH_2OH$ | Dimaleate.¼ $H_2O$ | 151–153 | IP |
| 36 | 6 | H | H | Et | Fumarate | 236–238 | M |
| 37 | 6 | 4-F | H | $CH_2CH_2OH$ | Dimaleate | 135–137 | A |
| 38 | 6 | 4-F | H |  | — | 167–168 | A-AT |

TABLE 12-continued
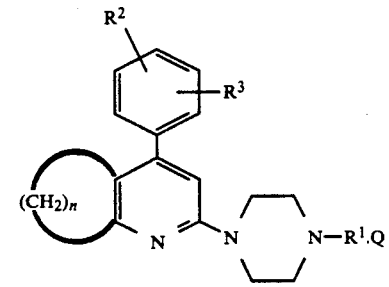
| Ex. | n | R² | R³ | R¹ | Q | M.p. (°C.) | Sol. recry. |
|---|---|---|---|---|---|---|---|
| 39 | 6 | 4-F | H | 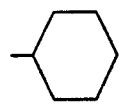 | — | 165–167 | M |
| 40 | 6 | 4-F | H | 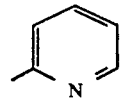 | — | 156–157 | A-AT |
| 41 | 6 | 4-F | H | 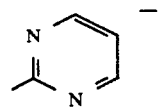 | — | 206–208 | M-AT |
| 42 | 6 | 3-F | H | Et | Dimaleate | 153–155 | A |
| 43 | 6 | 2-F | H | Et | Fumarate | 201–204 | A |
| 44 | 6 | 4-Cl | H | Et | — | 133–135 | CF-IP |
| 45 | 6 | 4-Cl | H | CH₂CH₂OH | — | 156–158 | CF-A |
| 46 | 6 | 3-Cl | H | Et | — | 114–115 | IP |
| 47 | 6 | 3-Cl | H | CH₂CH₂OH | Oxalate | 210–212 | M |
| 48 | 6 | 4-Br | H | Et | — | 134–136 | A |
| 49 | 6 | 4-OMe | H | Et | — | 113–114 | MC-HX |
| 50 | 6 | 4-OMe | H | CH₂CH₂OH | HCl.½ H₂O | 153–156 | A-E |
| 51 | 6 | 4-Me | H | Et | Dimaleate | 163–164 | A |
| 52 | 6 | 4-Me | H | CH₂CH₂OH | Oxalate | 207–209 | A |
| 53 | 6 | 4-F | 2-F | CH₂CH₂OH | Dioxalate.1/10 H₂O | 169–172 | A |
| 54 | 6 | 4-F | 3-F | Et | — | 105–106 | AC |
| 55 | 6 | 6-F | 2-F | Et | — | 104–105 | AC |
| 56 | 7 | 4-F | H | Et | Fumarate | 184–189 | A-E |
TABLE 13
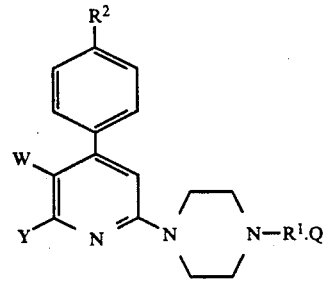
| Ex. | W Y | R² | R¹ | Q | M.p. (°C.) | Sol. recry. |
|---|---|---|---|---|---|---|
| 57 | 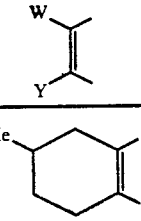 | H | Et | Dimaleate | 138–140 | A |

TABLE 13-continued

| Ex. | W/Y | $R^2$ | $R^1$ | Q | M.p. (°C.) | Sol. recry. |
|---|---|---|---|---|---|---|
| 58 | Me-cyclohexene | H | $CH_2CH_2OH$ | Dimaleate | 140–141 | A |
| 59 | Me-cyclohexene | F | Et | Dioxalate·¼ $H_2O$ | 126–127 | A |
| 60 | Me-cyclohexene | F | $CH_2CH_2OH$ | Fumarate | 160–161 | A |
| 61 | t-Bu-cyclohexene | H | Et | — | 130–131 | A |
| 62 | t-Bu-cyclohexene | H | $CH_2CH_2OH$ | — | 162–163 | A |
| 63 | Ph-cyclohexene | F | Et | Fumarate | 212–215 | M-A |
| 64 | Me-cyclohexene | F | Et | Dimaleate | 141–142 | IP |
| 65 | Me,Me-cyclohexene | F | $CH_2CH_2OH$ | Dimaleate·¼ $H_2O$ | 120–122 | A |
| 66 | Me,Me-cyclohexene | F | Et | Fumarate | 209–211 | M-A |
| 67 | Me,Me-cyclohexene | F | $CH_2CH_2OH$ | HCl | 200–203 | A-E |

TABLE 13-continued

[Structure: pyridine with R² on phenyl at 4-position, W and Y substituents, and piperazine-N-R¹·Q at 2-position]

| Ex. | W/Y group | R² | R¹ | Q | M.p. (°C.) | Sol. recry. |
|---|---|---|---|---|---|---|
| 68 | 4,4-diMe, 6-Me cyclohexenyl | F | Et | — | 107–108 | IP |
| 69 | 4,4-diMe, 6-Me cyclohexenyl | F | CH₂CH₂OH | Dioxalate.¼ H₂O | 125–126 | A |
| 70 | 6-Me, 3-iPr cyclohexenyl | F | Et | Fumarate | 203–204 | A |
| 71 | norbornenyl | H | Et | Dimaleate.¼ H₂O | 173–176 | A |
| 72 | norbornenyl | H | CH₂CH₂OH | Dimaleate | 140–142 | A |
| 73 | norbornenyl | F | Et | Dimaleate | 163–169 | IP |
| 74 | norbornenyl | F | CH₂CH₂OH | Dimaleate | 159–161 | A |
| 75 | bicyclic | F | Et | Fumarate | 234–236 | M-A |
| 76 | bicyclic | F | Et | Fumarate | 216–219 | M-A |

TABLE 13-continued

[Structure shown: pyridine ring substituted with R² on phenyl, W, Y positions, and piperazine N—R¹·Q group; with separate W/Y bicyclic fragment structure]

| Ex. | [W/Y structure] | R² | R¹ | Q | M.p. (°C.) | Sol. recry. |
|---|---|---|---|---|---|---|
| 77 | [bicyclic] | F | Et | Fumarate.½ H₂O | 226-230 | M-A |

EXAMPLES 78-85

In the same manner as described in Example 3 except that the corresponding starting materials are used, there are obtained the following compounds.

(Example 78)

2-(4-Methyl-1-homopiperazinyl)-4-(4-fluorophenyl)-6,7,8,9-tetrahydro-5H-cyclohepta[b]pyridine maleate, m.p. 187°-189° C. (ethanol)

(Example 79)

2-(4-Butanoyl-1-homopiperazinyl)-4-(4-fluorophenyl)-6,7,8,9-tetrahydro-5H-cyclohepta[b]pyridine, oily product (Example 80)

2-(4-Methyl-1-homopiperazinyl)-4-(4-fluorophenyl)-5,6,7,8,9,10-hexahydrocycloocta[b]pyridine dimaleate, m.p. 141°-143° C. (ethanol)

(Example 81)

2-(4-Benzoyl-1-homopiperazinyl)-4-(4-fluorophenyl)-5,6,7,8,9,10-hexahydrocycloocta[b]pyridine, oily product (Example 82)

2-[4-(2-Methoxyethyl)-1-piperazinyl]-4-(4-fluorophenyl)-5,6,7,8,9,10-hexahydrocycloocta[b]pyridine dimaleate, m.p. 119°-120° C. (acetonitrile)

(Example 83)

2-(3-Methyl-1-piperazinyl)-4-(4-fluorophenyl)-5,6,7,8,9,10-hexahydrocycloocta[b]pyridine, m.p. 138°-141° C. (isopropyl alcohol-hexane)

(Example 84)

2-(3,5-Dimethyl-1-piperazinyl)-4-(4-fluorophenyl)-5,6,7,8,9,10-hexahydrocycloocta[b]pyridine ½ fumarate, m.p. 262°-266° C. (decomposed) (methanol)

(Example 85)

2-(1-Homopiperazinyl)-4-(4-fluorophenyl)-5,6,7,8,9,10-hexahydrocycloocta[b]pyridine maleate, m.p. 198°-200° C. (ethanol)

EXAMPLE 86

Preparation of 2-(1-piperazinyl)-4-phenyl-5,6,7,8-tetrahydroquinoline

A mixture of 2-(4-benzyl-1-piperazinyl)-4-phenyl-5,6,7,8-tetrahydroquinoline (m.p. 105°-107° C., 2.1 g) obtained in the same manner as in Example 3, chloroethyl chloroformate (0.86 g) and methylene chloride (40 ml) is refluxed for 1 hour. The reaction mixture is concentrated under reduced pressure, and methanol (40 ml) is added to the residue. The mixture is refluxed for 30 minutes and concentrated under reduced pressure. The resulting residue is dissolved in water, washed with diethyl ether, neutralized with potassium carbonate, and extracted with chloroform. The extract is washed with water, dried over anhydrous sodium sulfate, and the solvent is distilled off under reduced pressure. To the residue is added a solution of maleic acid in ethanol. The resulting maleate product is recrystallized from ethanol to give the dimaleate of the desired product (1.2 g), m.p. 150°-151° C.

EXAMPLES 87-110

In the same manner as described in Example 86 except that the corresponding starting materials are used, there are obtained the compounds as shown in Tables 14 and 15.

TABLE 14

[Structure: phenyl with R²/R³ substituents attached to pyridine fused with (CH₂)ₙ ring, 2-position bearing piperazinyl-H·Q]

| Ex. | n | R² | R³ | Q | Melting point (°C.) | Solvent for recrystaln. |
|---|---|---|---|---|---|---|
| 87 | 3 | H | H | Maleate | 175-179 | A |
| 88 | 3 | 4-F | H | Dimaleate | 152-155 | A |

TABLE 14-continued (structure with (CH₂)ₙ ring, R², R³ substituted phenyl, piperazinyl-H.Q)

| Ex. | n | R² | R³ | Q | Melting point (°C.) | Solvent for recrystaln. |
|---|---|---|---|---|---|---|
| 89 | 3 | 3-F | H | Maleate | 176–179 | A |
| 90 | 3 | 2-F | H | Maleate | 186–188 | A |
| 91 | 3 | 4-OMe | H | Dimaleate | 148–149 | A |
| 92 | 4 | 4-F | H | Dimaleate.¼ H₂O | 143–145 | A |
| 93 | 4 | 3-F | H | Dimaleate.¼ H₂O | 148–151 | A |
| 94 | 4 | 2-F | H | Dimaleate | 136–137 | A |
| 95 | 4 | 4-OMe | H | Dioxalate.¼ H₂O | 210–213 | M |
| 96 | 5 | H | H | Maleate | 173–176 | A |
| 97 | 5 | 4-F | H | Dimaleate | 144–147 | A |
| 98 | 5 | 3-F | H | Maleate | 173–175 | A |
| 99 | 5 | 2-F | H | Maleate | 173–180 | A |
| 100 | 5 | 4-Cl | H | Maleate.¼ H₂O | 176–178 | M-A |
| 101 | 5 | 4-OMe | H | Dimaleate | 133–137 | IP |
| 102 | 5 | 4-Me | H | Dimaleate.¾ H₂O | 95–97 | IP |
| 103 | 6 | H | H | Dimaleate.¼ H₂O | 124–127 | A |
| 104 | 6 | 4-F | H | Maleate | 186–190 | A |
| 105 | 6 | 4-Me | H | Fumarate | 218–221 | A |
| 106 | 6 | 4-F | 2-F | ½ Fumarate.¼ H₂O | 177–179 | A |

TABLE 15

(structure with W, Y substituted pyridine, R² phenyl, piperazinyl-H.Q)

| Ex. | W, Y group | R² | Q | Melting point (°C.) | Solvent for recrystaln. |
|---|---|---|---|---|---|
| 107 | norbornane-fused | H | Dimaleate.¼ H₂O | 147–149 | A |
| 108 | Me-cyclohexane-fused | H | 3/2 Oxalate.¼ H₂O | 178–181 | M |
| 109 | Me-cyclohexane-fused | F | ½ Fumarate.1/10 H₂O | 181–186 | A |
| 110 | t-Bu-cyclohexane-fused | H | Maleate | 207–208 | A |

EXAMPLE 111

Preparation of 2-(4-methyl-1-piperazinyl)-4-(4-fluorophenyl)-6,7-dihydro-5H-1-pyrindine A mixture of 2-(1-piperazinyl)-4-(4-fluorophenyl)-6,7-dihydro-5H-1-pyrindine (2 g), 37% aqueous formaldehyde solution (0.66 g), formic acid (0.68 g) and water (15 ml) is refluxed for 20 minutes. After cooling, the reaction mixture is made alkaline with diluted aqueous sodium hydroxide solution, and extracted with ethyl acetate. The extract is washed with water, dried over anhydrous sodium sulfate, and concentrated under reduced pressure. To the residue is added a solution of maleic acid in ethanol, and the resulting maleate product is recrystallized from ethanol to give the maleate of the desired compound, m.p. 135°-137° C.

EXAMPLES 112-117

In the same manner as described in Example 111 except that the corresponding starting materials are used, there are obtained the following compounds.

(Example 112)

2-(4-Methyl-1-piperazinyl)-4-(4-fluorophenyl)-5,6,7,8,9,10-hexahydrocycloocta[b]pyridine dimaleate, m.p. 136°-138° C. (ethanol)

(Example 113)

2-(4-Methyl-1-piperazinyl)-4-(4-methylphenyl)-5,6,7,8,9,10-hexahydrocycloocta[b]pyridine dimaleate, m.p. 152°-154° C. (ethanol)

(Example 114)

2-(4-Methyl-1-piperazinyl)-4-(2,4-difluorophenyl)-5,6,7,8,9,10-hexahydrocycloocta[b]pyridine, m.p. 132°-133° C. (ethanol)

(Example 115)

2-(4-Methyl-1-piperazinyl)-4-(4-fluorophenyl)-6-methyl-5,6,7,8-tetrahydroquinoline dimaleate, m.p. 161°-164° C. (ethanol)

(Example 116)

2-(3,4-Dimethyl-1-piperazinyl)-4-(4-fluorophenyl)-5,6,7,8,9,10-hexahydrocycloocta[b]pyridine fumarate ¼ hydrate, m.p. 173°-175° C. (ethanol-diethyl ether)

(Example 117)

2-(cis-3,5-Dimethyl-4-methyl-1-piperazinyl)-4-(4-fluorophenyl)-5,6,7,8,9,10-hexahydrocycloocta[b]pyridine fumarate, m.p. 208°-210° C. (methanol-ethanol)

EXAMPLE 118

Preparation of 2-(4-n-propyl-1-piperazinyl)-4-(4-fluorophenyl)-5,6,7,8,9,10-hexahydrocycloocta[b]pyridine A mixture of 2-(1-piperazinyl)-4-(4-fluorophenyl)-5,6,7,8,9,10-hexahydrocycloocta[b]pyridine (1.4 g), n-propyl bromide (0.56 g), potassium carbonate (0.68 g), potassium iodide (0.1 g) and methanol (50 ml) is refluxed for 15 hours. The reaction mixture is concentrated under reduced pressure and thereto is added water. The mixture is extracted with ethyl acetate, washed with water, dried over anhydrous sodium sulfate, and the solvent is distilled off under reduced pressure. To the residue is added a solution of maleic acid in ethanol, and the resulting maleate product is recrystallized from ethanol to give the dimaleate of the desired compound (0.6 g), m.p. 149°-152° C.

EXAMPLES 119-126

In the same manner as described in Example 118 except that the corresponding starting materials are used, there are obtained the compounds as shown in the following Table 16.

TABLE 16

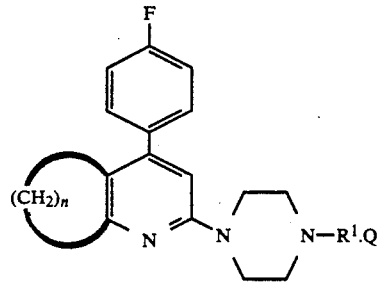

| Ex. | n | R¹ | Q | M.p. (°C.) | Solvent, for recrystal. |
|---|---|---|---|---|---|
| 119 | 3 | —(CH$_2$)$_3$OH | Maleate | 174–178 | A |
| 120 | 3 | —CH(Me)Me | Maleate | 215–218 | A |
| 121 | 6 | —CH(Me)Me | Dimaleate | 154–155 | A |
| 122 | 6 | —(CH$_2$)$_3$CH$_3$ | — | 89–90 | A |
| 123 | 6 | —(CH$_2$)$_4$CH$_3$ | Maleate | 213–217 | A-M |
| 124 | 6 | —(CH$_2$)$_5$CH$_3$ | Maleate | 196–197 | A |
| 125 | 6 | —CH$_2$CH=CH$_2$ | ¼ H$_2$O | 109–110 | AC |
| 126 | 6 | —CH$_2$C≡CH | — | 75–77 | HX |

EXAMPLE 127

Preparation of 2-(4-n-propyl-1-piperazinyl)-4-(2,4-difluorophenyl)-5,6,7,8,9,10-hexahydrocycloocta[b]pyridine In the same manner as described in Example 118 except that the corresponding starting materials are used, the desired product is obtained, m.p. 108°-109° C. (ethanol).

EXAMPLE 128

Preparation of 2-[4-(2-furoyl)-1-piperazinyl]-4-phenyl-5,6,7,8-tetrahydroquinoline A mixture of 2-(1-piperazinyl)-4-phenyl-5,6,7,8-tetrahydroquinoline (1.2 g), 2-furancarboxylic acid (0.46 g), chloroform (40 ml) and 1-(3-dimethylaminopropyl)-3-ethylcarbodiimide hydrochloride (0.79 g) is stirred at 25° C. for 2 hours. The reaction mixture is washed with water, dried over anhydrous sodium sulfate, and the solvent is distilled off under reduced pressure. The residue is dissolved in toluene and subjected to silica gel column chromatography. The fractions eluted with toluene and toluene-ethyl acetate (9:1) are collected and recrystallized from ethanol to give the desired product (0.4 g), m.p. 128°-130° C.

EXAMPLE 129

Preparation of 2-[4-(2-furoyl)-1-piperazinyl]-4-(4-fluorophenyl)-6,7-dihydro-5H-1-pyrindine In the same manner as described in Example 128 except that the corresponding starting materials are used, the desired product is obtained, m.p. 165°-166° C. (ethanol).

EXAMPLE 130

Preparation of
2-(4-ethyl-1-piperazinyl)-4-(4-hydroxyphenyl)-
5,6,7,8,9,10-hexahydrocycloocta[b]pyridine 2-(4-Ethyl-1-piperazinyl)-4-(4-methoxyphenyl)-5,6,7,8,9,10-hexahydrocycloocta[b]pyridine (1.3 g) is dissolved in 48% hydrobromic acid (10 ml) and the mixture is stirred at 120° C. for 2 hours. After cooling, water is added thereto and the mixture is neutralized with 1N aqueous sodium hydroxide solution and sodium hydrogen carbonate. The resulting precipitate is collected by filtration, washed with water, and recrystallized from methanol to give the desired product (0.6 g), m.p. 250°–253° C.

EXAMPLE 131

Preparation of
2-(4-ethyl-1-piperazinyl)-4-(2,4-difluorophenyl)-6,7,8,9-tetrahydro-5H-cyclohepta[b]pyridine In the same manner as described in Example 3 except that the corresponding starting materials are used, there is obtained the oxalate ·½ hydrate of the desired product, m.p. 225°–227° C. (methanol).

EXAMPLE 132

Preparation of
2-(4-ethyl-1-piperazinyl)-4-(2,4-difluorophenyl)-6,7-dihydro-5H-1-pyrindine In the same manner as described in Example 3 except that the corresponding starting materials are used, there is obtained the maleate of the desired product, m.p. 195°–196° C. (ethanol).

EXAMPLE 133

Preparation of
2-(4-cyclopropyl-1-piperazinyl)-4-(4-fluorophenyl)-5,6,7,8,9,10-hexahydrocycloocta[b]pyridine In the same manner as described in Example 3 except that the corresponding starting materials are used, there is obtained the desired product, m.p. 125°–128° C. (ethanol).

EXAMPLE 134

Preparation of
2-[4-(4-fluorophenyl)-1-piperazinyl]-4-(4-fluorophenyl)-5,6,7,8,9,10-hexahydrocycloocta[b]pyridine In the same manner as described in Example 3 except that the corresponding starting materials are used, there is obtained the desired product, m.p. 130°–131° C. (methanol).

EXAMPLE 135

Preparation of
2-(4-ethyl-1-piperazinyl)-4-(2,4-difluorophenyl)-5,6,7,8-tetrahydro-5,8-methanoquinoline In the same manner as described in Example 3 except that the corresponding starting materials are used, there is obtained the oxalate ·½ hydrate of the desired product, m.p. 234°–238° C. (ethanol).

EXAMPLE 136

Preparation of
2-(cis-3,5-dimethyl-4-methyl-1-piperazinyl)-4-(4-fluorophenyl)-6,7-dihydro-5H-1-pyrindine In the same manner as described in Example 111 except that the corresponding starting materials are used, there is obtained the fumarate ·¼ hydrate of the desired product, m.p. 204°–208° C. (methanol-ethanol).

EXAMPLE 137

Preparation of
2-{4-[3-(4-fluorobenzoyl)propyl]-1-piperazinyl}-4-(4-fluorophenyl)-6,7-dihydro-5H-1-pyrindine In the same manner as described in Example 118 except that the corresponding starting materials are used, there is obtained the desired product, m.p. 115°–116° C. (ethanol).

EXAMPLE 138

Preparation of
2-[4-(3-hydroxypropyl)-1-piperazinyl]-4-(4-fluorophenyl)-5,6,7,8,9,10-hexahydrocycloocta[b]pyridine In the same manner as described in Example 118 except that the corresponding starting materials are used, there is obtained the dioxalate ·¼ hydrate of the desired product, m.p. 136°–138° C. (methanol).

EXAMPLE 139

Preparation of
2-[4-(2-acetoxyethyl)-1-piperazinyl]-4-(4-fluorophenyl)-5,6,7,8,9,10-hexahydrocycloocta[b]pyridine A mixture of 2-[4-(2-hydroxyethyl)-1-piperazinyl]-4-(4-fluorophenyl)-5,6,7,8,9,10-hexahydrocycloocta[b]pyridine (1.5 g), acetic anhydride (0.6 g), triethylamine (0.7 g) and ethyl acetate (30 ml) is refluxed for 2 hours. After cooling, the reaction mixture is washed with water, dried over anhydrous sodium sulfate, and concentrated under reduced pressure. The residue is dissolved in toluene and the mixture is subjected to silica gel column chromatography. The fractions eluted with toluene and toluene-ethyl acetate (1:1) are collected and thereto is added a solution of maleic acid in ethanol. The resulting maleate product is recrystallized from ethanol to give the maleate of the desired product (0.65 g), m.p. 187°–191° C.

EXAMPLE 140

Preparation of
2-(4-cyclopropylmethyl-1-piperazinyl)-4-(4-fluorophenyl)-5,6,7,8,9,10-hexahydrocycloocta[b]pyridine In the same manner as described in Example 118 except that the corresponding starting materials are used, there is obtained the desired product, m.p. 109°–110° C. (methylene chloride-hexane).

The preparation of the pharmaceutical composition of the present invention is illustrated by the following Preparations.

| Preparation 1 Preparation of capsules: | |
|---|---|
| Components | Amount |
| 2-(4-Ethyl-1-piperazinyl)-4-(4-fluorophenyl)-6,7,8,9-tetrahydro-5H-cyclohepta[b]pyridine dimaleate | 5 g |

-continued

Preparation 1
Preparation of capsules:

| Components | Amount |
| --- | --- |
| Corn starch | 57 g |
| Lactose | 10 g |
| Crystalline cellulose | 25 g |
| Hydroxypropyl cellulose | 2 g |
| Light silicic anhydride | 0.5 g |
| Magnesium stearate | 0.5 g |

According to a conventional method, the above components are mixed and granulated, and the granules thus obtained are packed in capsules (1000 capsules) to give capsules containing the granules of 100 mg per one capsule.

Preparation 2
Preparation of tablets:

| Components | Amount |
| --- | --- |
| 2-(4-Ethyl-1-piperazinyl)-4-(4-fluorophenyl)-5,6,7,8,9,10-hexahydrocycloocta[b]pyridine dimaleate | 5 g |
| Corn starch | 20 g |
| Lactose | 30 g |
| Crystalline cellulose | 30 g |
| Hydroxypropyl cellulose | 5 g |
| Low sustituted hydroxypropyl cellulose | 10 g |

According to a conventional method, the above components are mixed and granulated, and the granules thus obtained are mixed with light silicic anhydride and magnesium stearate, and the mixture is tabletted to give tablets containing the active ingredient of 5 mg per one tablet.

Preparation 3
Preparation of powders:

| Components | Amount |
| --- | --- |
| 2-(4-Ethyl-1-piperazinyl)-4-(4-fluorophenyl)-5,6,7,8,9,10-hexahydrocycloocta[b]pyridine dimaleate | 5 g |
| Corn starch | 173 g |
| Lactose | 300 g |
| Hydroxypropyl cellulose | 20 g |

According to a conventional method, the above components are mixed, granulated and screened, and the granules thus obtained are mixed with an appropriate amount of light silicic anhydride to give powders (100 triturations).

Preparation 4
Preparation of injections:

| Components | Amount |
| --- | --- |
| 2-(4-Ethyl-1-piperazinyl)-4-(4-fluorophenyl)-5,6,7,8,9,10-hexahydrocycloocta[b]pyridine dimaleate | 5 g |
| D-Sorbitol | 45 g |
| 1N Aqueous solution of maletic acid or sodium hydroxide | q.s. |
| Distilled water for injection | q.s. |
| Totally | 1000 ml |

The above active ingredient and D-sorbitol are mixed with distilled water for injection, and thereto is added 1N aqueous solution of maletic acid or sodium hydroxide to adjust the solution to pH 4.0. The solution is filterd with a membrane filter (pore size, 0.22 μm) and packed in ampoule (content 10 ml). The ampoule is sealed by melting and sterilized with high pressure steam at 121° C. for 20 minutes to give injection solutions.

Preparation 5
Preparation of lyophilized preparation:

| Components | Amount |
| --- | --- |
| 2-(4-Ethyl-1-piperazinyl)-4-(4-fluorophenyl)-5,6,7,8,9,10-hexahydrocycloocta[b]pyridine dimaleate | 5 g |
| D-Mannitol | 45 g |
| 1N Aqueous solution of maleic acid of sodium hydroxide | q.s. |
| Distilled water for injection | q.s. |
| Totally | 1000 ml |

The above active ingredient and D-mannitol are mixed with distilled water for injection, and thereto is added 1N aqueous solution of maleic acid or sodium hydroxide to adjust the solution to pH 4.0. The solution is filtered with a membrane filter (pore size, 0.22 μm) and packed in a vial (content 10 ml). The vial is sealed with a rubber stopper in halfway and subjected to lyophilization, that is, pre-freezing, primary drying at −50° C., secondary drying at −20° C., and then final drying at 20° C. After completely sealed with a rubber stopper within a chamber, the vial is covered with a flip-off cap to give a lyophilized preparation.

What is claimed is:

1. A compound of the formula (I):

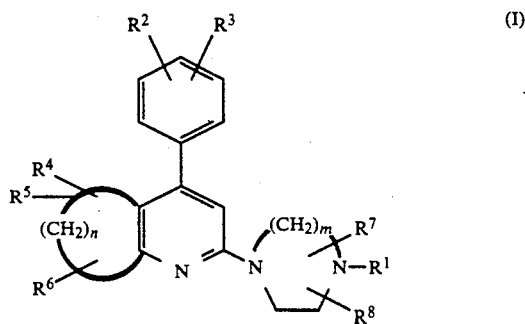

wherein n is 3, 4, 5, 6 or 7, $R^1$ is a hydrogen atom, $C_1$-$C_{10}$ alkyl, $C_2$-$C_6$ alkenyl, $C_2$-$C_6$ alkynyl, $C_3$-$C_8$ cycloalkyl, $C_3$-$C_6$ cycloalkyl-($C_1$-$C_4$) alkyl, hydroxy-($C_2$-$C_6$) alkyl, $C_1$-$C_3$ alkoxy-($C_2$-$C_6$) alkyl, $C_1$-$C_4$ alkanoyloxy ($C_2$-$C_6$) alkyl, $C_5$-$C_6$ cycloalkylcarbonyloxy ($C_2$-$C_6$) alkyl, benzoyloxy ($C_2$-$C_6$) alkyl which is optionally substituted by halogen, $C_1$-$C_3$ alkyl or $C_1$-$C_3$ alkoxy, furoyloxy ($C_2$-$C_6$) alkyl, thenoyloxy ($C_2$-$C_6$) alkyl, pyridylcarbonyloxy ($C_2$-$C_6$)alkyl, pyrimidylcarbonyloxy ($C_2$-$C_6$) alkyl or isoquinolylcarbonyloxy ($C_2$-$C_6$) alkyl, a benzoyl or naphthyloyl ($C_1$-$C_6$) alkyl group which is optionally mono- or disubstituted on the phenyl or naphthyl ring by substituents(s) selected from the group consisting of halogen, $C_1$-$C_3$ alkyl, $C_1$-$C_3$ alkoxy and trifluoromethyl, a phenyl or napthyl group which is optionally mono- or disubstituted by substituent(s) selected from the group consisting of halogen, $C_1$-$C_3$ alkyl, $C_1$-$C_3$ alkoxy and trifluoromethyl, furyl, thienyl, pyridyl, pyrimidyl or isoquinolyl, $C_1$-$C_4$ alkanoyl, $C_5$-$C_6$ cycloalkylcarbonyl, a benzoyl group which is optionally substituted by halogen, $C_1$-$C_3$ alkyl or $C_1$-$C_3$ alkoxy, furoyl, thenoyl, pyridylcarbonyl, pyrimidylcarbonyl or isoquinolylcarbonyl, $R^2$ and $R^3$ are the same or different and are each a hydrogen atom, a halogen atom, $C_1$-$C_6$ alkyl, $C_1$-$C_6$ alkoxy, trifluoromethyl, or hydroxy, $R^4$, $R^5$ and $R^6$ are the same or different and are each a hydrogen atom, $C_1$-$C_6$ alkyl, or phenyl, or two of $R^4$, $R^5$ and $R^6$ combine to form a single bond or $C_1$-$C_3$ alkylene, $R^7$ and $R^8$ are the same or different and are each a hydrogen atom or $C_1$-$C_3$ alkyl, m is 2 or 3, or an acid addition salt thereof.

2. A compound according to claim 1, wherein $R^1$ is a hydrogen atom, $C_1$-$C_{10}$ alkyl, $C_3$-$C_8$ cycloalkyl, hydroxy-($C_2$-$C_6$) alkyl, $C_1$-$C_3$ alkoxy-($C_2$-$C_4$) alkyl, $C_2$-$C_4$ alkanoyloxy-($C_2$-$C_6$) alkyl, a benzoyl-($C_2$-$C_5$) alkyl group in which the phenyl moiety may optionally be substituted by halogen, $C_1$-$C_3$ alkyl or $C_1$-$C_3$ alkoxy, $C_2$-$C_4$ alkenyl, $C_2$-$C_4$ alkynyl, pyridyl, pyrimidyl, $C_2$-$C_5$ alkanoyl or furoyl, $R^2$ and $R^3$ are the same or different and are each a hydrogen atom, a halogen atom, methyl or methoxy, $R^4$, $R^5$ and $R^6$ are the same or different and are each a hydrogen atom or $C_1$-$C_4$ alkyl, or two of them combine to form $C_1$-$C_2$ alkylene, $R^7$ and $R^8$ are the same or different and are each or differently a hydrogen atom or $C_1$-$C_3$ alkyl, m is 2, or an acid addition salt thereof.

3. A compound according to claim 2, wherein $R^1$ is a hydrogen atom, $C_1$-$C_8$ alkyl, $C_3$-$C_8$ cycloalkyl, hydroxy-($C_2$-$C_6$) alkyl, $C_1$-$C_2$ alkoxy-($C_2$-$C_3$)alkyl, acetyloxy-($C_2$-$C_4$) alkyl, $C_3$-$C_4$ alkenyl or $C_2$-$C_3$ alkanoyl, $R^2$ and $R^3$ are the same or different and are each a hydrogen atom or a halogen atom, or one of them is a hydrogen atom and another one is a halogen atom, methyl or methoxy, or an acid addition salt thereof.

4. A compound according to claim 3, wherein $R^2$ and $R^3$ are the same or different and are each hydrogen atom or a fluorine atom, or an acid addition salt thereof.

5. A compound of the formula:

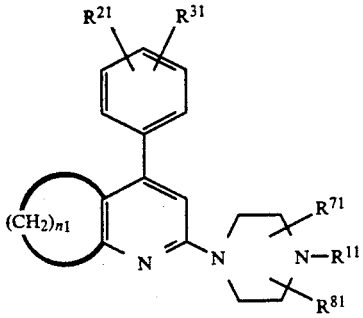

wherein $n_1$ is 3, 6 or 7, $R^{11}$ is a hydrogen atom, $C_1$-$C_8$ alkyl, $C_3$-$C_6$ cycloalkyl, hydroxy-($C_2$-$C_4$) alkyl, $C_1$-$C_2$ alkoxy-($C_2$-$C_3$) alkyl or $C_3$ alkenyl, $R^{21}$ and $R^{31}$ are the same or different and are each a hydrogen atom or fluorine atom, $R^{71}$ and $R^{81}$ are the same or different and are each a hydrogen atom or $C_1$-$C_3$ alkyl, or an acid addition salt thereof.

6. A compound according to claim 1, which is a compound of the formula:

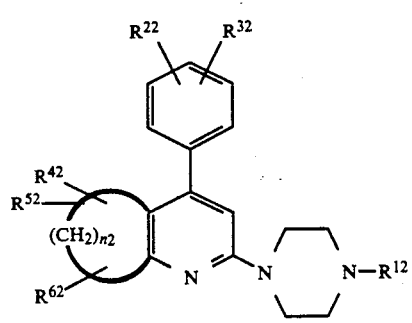

wherein $n_2$ is 4 or 5, $R^{12}$ is a hydrogen atom, $C_1$-$C_8$ alkyl, $C_3$-$C_8$ cycloalkyl, hydroxy-($C_2$-$C_4$) alkyl, $C_1$-$C_2$ alkoxy-($C_2$-$C_3$) alkyl or $C_3$ alkenyl, $R^{22}$ and $R^{32}$ are the same or different and are each a hydrogen atom or fluorine atom, $R^{42}$, $R^{52}$ and $R^{62}$ are the same or different and are each a hydrogen atom or $C_1$-$C_4$ alkyl, or two of them combine to form $C_1$-$C_2$ alkylene, or an acid addition salt thereof.

7. A compound according to claim 5, wherein $n_1$ is 6, $R^{11}$ is $C_1$-$C_6$ alkyl, $C_3$-$C_6$ cycloalkyl or hydroxy($C_2$-$C_4$) alkyl, $R^{21}$ and $R^{31}$ are the same or different and are each a hydrogen atom or a fluorine atom substituted at 2- or 4-position of the phenyl ring, $R^{71}$ and $R^{81}$ are each a hydrogen atom, or an acid addition salt thereof.

8. A compound according to claim 6, wherein $n_2$ is 5, $R^{12}$ is $C_1$-$C_6$ alkyl, $C_3$-$C_6$ cycloalkyl or hydroxy($C_2$-$C_4$) alkyl, $R^{22}$ and $R^{32}$ are the same or different and are each a hydrogen atom or a fluorine atom substituted at 2- or 4-position of the phenyl ring, $R^{42}$, $R^{52}$ and $R^{62}$ are all hydrogen atoms, or two of them combine to form $C_1$-$C_2$ alkylene and the other is a hydrogen atom, or an acid addition salt thereof.

9. A compound according to claim 5, which is a compound of the formula:

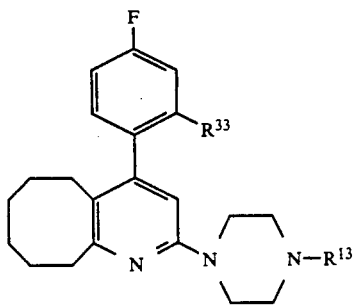

wherein $R^{13}$ is methyl, ethyl, propyl, butyl, pentyl or hydroxyethyl, $R^{33}$ is a hydrogen atom or a fluorine atom, or an acid addition salt thereof.

10. 2-(4-Ethyl-1-piperazinyl)-4-(4-fluorophenyl)-5,6,7,8,9,10-hexahydrocycloocta[b]pyridine, or an acid addition salt thereof.

11. 2-(4-Ethyl-1-piperazinyl)-4-(2,4-difluorophenyl)-5,6,7,8,9,10-hexahydrocycloocta[b]pyridine, or an acid addition salt thereof.

12. 2-(4-n-Propyl-1-piperazinyl)-4-(4-fluorophenyl)-5,6,7,8,9,10-hexahydrocycloocta[b]pyridine, or an acid addition salt thereof.

13. 2-(4-Methyl-1-piperazinyl)-4-(4-fluorophenyl)-5,6,7,8,9,10-hexahydrocycloocta[b]pyridine, or an acid addition salt thereof.

14. 2-(4-Methyl-1-piperazinyl)-4-(2,4-difluorophenyl)-5,6,7,8,9,10-hexahydrocycloocta[b]pyridine, or an acid addition salt thereof.

15. A psychotropic composition comprising as an active ingredient an efficient amount of the compound of the formula (I) as set forth in claim 1, or a pharmaceutically acceptable salt thereof in admixture with a pharmaceutically acceptable carrier or diluent.

16. A composition according to claim 15, wherein the active ingredient is the compound as set forth in claim 5, or a pharmaceutically acceptable salt thereof.

17. A composition according to claim 15, wherein the active ingredient is the compound as set forth in claim 6, or a pharmaceutically acceptable salt thereof.

18. A composition according to claim 15, wherein the active ingredient is the compound as set forth in claim 9, or a pharmaceutically acceptable salt thereof.

19. A method for treatment of psychotic diseases, which comprising administering an effective amount of a compound of the formula (I) as set forth in claim 15 to a patient suffered from psychotic diseases.

* * * * *